(12) United States Patent
Jaquish et al.

(10) Patent No.: US 7,775,937 B2
(45) Date of Patent: Aug. 17, 2010

(54) SYSTEMS AND METHODS FOR ADMINISTERING AN EXERCISE PROGRAM

(75) Inventors: John Paul Jaquish, Nevada City, CA (US); Paul Edward Jaquish, Nevada City, CA (US)

(73) Assignee: Performance Health Systems, LLC, Nevada City, CA (US)

( * ) Notice: Subject to any disclaimer, the term of this patent is extended or adjusted under 35 U.S.C. 154(b) by 0 days.

(21) Appl. No.: 12/533,607

(22) Filed: Jul. 31, 2009

(65) Prior Publication Data

US 2010/0137108 A1    Jun. 3, 2010

(51) Int. Cl.
   A63B 71/00    (2006.01)
(52) U.S. Cl. .................... 482/8; 482/1; 482/9; 434/247
(58) Field of Classification Search ................. 482/1–9, 482/51, 900–902; 434/247–259; 601/23; 73/379.01–379.03
   See application file for complete search history.

(56) References Cited

U.S. PATENT DOCUMENTS

| | | | |
|---|---|---|---|
| 4,571,682 A * | 2/1986 | Silverman et al. ........... 600/301 |
| 6,582,342 B2 * | 6/2003 | Kaufman ....................... 482/8 |
| 7,070,539 B2 * | 7/2006 | Brown et al. ................... 482/8 |
| 7,182,719 B2 * | 2/2007 | Tuller .......................... 482/140 |
| 7,717,825 B2 * | 5/2010 | Van Der Hoeven ............ 482/8 |
| 2002/0091039 A1 * | 7/2002 | Reinbold et al. ............... 482/1 |

\* cited by examiner

*Primary Examiner*—Glenn Richman
(74) *Attorney, Agent, or Firm*—Jones Day; Brett A. Lovejoy

(57) ABSTRACT

Systems and methods for facilitating an isometric contraction exercise regimen for many subjects across a network are provided. One or more exercise constraints are developed for a subject as a function of the medical health information of the subject. The subject performs a plurality of isometric contraction exercises using exercise equipment always in the presence of a personal fitness trainer thereby producing an exercise result. The exercise equipment has a strain gauge in order to impose exercise constraints in the one or more exercise constraints. A mandatory recovery period for the subject is then imposed. During this mandatory recovery period, the subject does not perform isometric contraction exercises. These steps are repeated using a new set of one or more exercise constraints that were refined based upon the exercise result of a previous isometric contraction exercise work out session.

18 Claims, 15 Drawing Sheets

PERFORMANCE
HEALTH
SYSTEMS

Exerciser 4

Start Date: 2/3/2005   Report Date: 9/18/2005 4:59 PM

Full Body Strength Increase: 86%

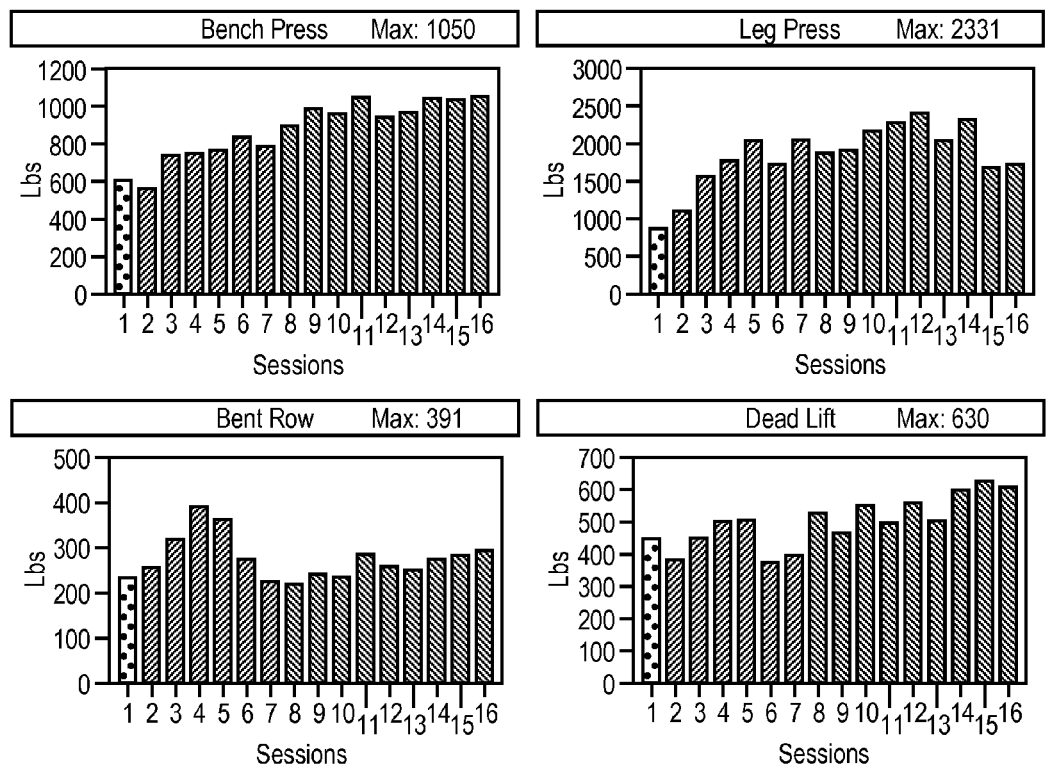

Analysis and Recommendations:

You are making progress in the Bench Press and in the Row, however no progress in the Leg Press and the Deadlift. This isn't necessarily a common situation due to the Leg Press and Deadlift utilizing larger muscle groups, they are usually the last groups to indicate overtraining. This situation doesn't indicate overtraining and could possibly indicate a back soreness or injury. If this trend continues it would be advisable to look at some of the activities that you partake in during an average week that could be exhausting your lower back. SUGGESTION: Stay on current recovery schedule.

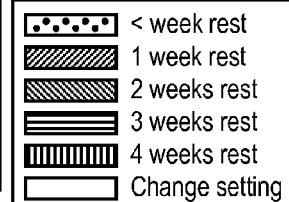

Next Appointment: Thursday 9/29/205 at 13:45

FIG. 6D

SYSTEMS AND METHODS FOR ADMINISTERING AN EXERCISE PROGRAM

FIELD OF THE INVENTION

The field of the present invention relates to the systems and methods used to facilitate an isometric contraction exercise program for subjects interested in improving their health and fitness.

BACKGROUND OF THE INVENTION

Experts in the field of sports medicine have identified the increasing problem of exercise related injuries. G. O. Matheson, MD, Ph.D., and editor of *The Physician and Sports Medicine*, wrote "Almost two decades ago, great attention was paid to physical fitness, technique, and equipment design as protective against injury. Hopes were high that these measures would reduce injuries. Yet according to recent statistics, the incidence of injuries is at an all time high." As an example, the *U.S. Consumer Product Safety Commission*, 2001, reported a continuing and escalating increase in sports/exercise participation due to the baby boomer demographics. Not surprisingly, there has been a coincident increase in sports/exercise related injuries. This same report documents sports and exercise injuries in the age group 35 to 54 increasing about thirty-three percent between 1991 and 1998. Furthermore, recently released Frost and Sullivan Fitness Industry Statistics show the phenomenal growth of people over 55 in fitness almost suggesting an emerging branch of "geriatric sports medicine."

Existing fitness programs' lack of sustainability is also an increasing problem in the fitness industry. Less than five percent of the United States population consistently maintains strength and fitness throughout their adult life. A multitude of fitness programs and centers have been developed and literally countless fitness products have been promoted over the past 30 years, but many of these programs have largely been unsatisfactory. *Fitness Management Magazine*, 2005 published Frost & Sullivan data stating that the average home exercise equipment is used for only one year, and the average fitness center membership lasts only two years. These disappointing statistics support the argument that the fitness industry needs a new solution with safety, longevity and sustainability as its primary goal.

Moreover, almost without exception the fitness industry has underestimated the importance of allowing time for tissue recovery. As a result, the potential benefits of exercise participation are often reduced and the chances of injury are increased. Furthermore, today's fitness industry does not even generate or collect the type of data needed to calculate proper recovery periods, let alone have the equipment or business method and system to support it. The condition of the fitness industry is such that accurate data and repeatable data are not available. Industry sources report that fitness equipment, in general, is not accurate within fifty percent. Some manufactures are even clearer, e.g., "makes no representations or warranties of any kind, with respect to merchantability of fitness or suitability for any general or particular purpose, or of the results anticipated or experienced in the use of such equipment, specifically including but not limited to the accuracy or inaccuracy of any data provided by the equipment."

The failure of existing fitness programs is clear and is evidenced by the fact that even the most dedicated fitness enthusiasts will often fail in their efforts to maintain fitness and strength. Common reasons for failure include schedule conflicts with personal and professional commitments, poorly contrived exercise routines producing disappointingly slow or limited progress, the inherent limitations of existing home exercise equipment, the often-overwhelming inconvenience or inadequacy of the local fitness facility, and perhaps the most serious, frequent and disabling injuries.

Given the above background, what is needed in the art are improved systems and methods for implementing exercise programs.

SUMMARY OF THE INVENTION

One aspect of the present invention provides an improved exercise program designed to increase individuals' strength and overall fitness while minimizing the number of exercise-related injuries they may suffer in the process. Provided are components that collectively decrease the number of exercise related injuries. Such components include, but are not limited to, (i) isometric contraction exercises that utilize custom designed, solid state exercise equipment; (ii) mandatory recovery periods between equipment use; (iii) collection of medical and physiological information before exercise participation; (iv) collection of the exercise results and the use of such data to calculate an appropriate recovery time; (v) central processing of an exerciser's incremental exercise results for the purpose of performance tracking as well as the calculation of mandatory recovery periods; and (vii) provision of timely feedback and recommendations for customization of individualized exercise programs. These components work together to produce an individualized, optimized, and safe muscle tissue development and fitness program, termed an isometric contraction model, in accordance with an aspect of the present invention.

As noted above, an aspect of the present invention makes use of a mandatory recovery period. Among other advantages, this mandatory recovery period prevents injuries, and optimizes the body's ability to develop skeletal muscle. Rest and recovery are essential to injury free, successful exercise. This is particularly true in strength building. Berardi and Mejia, in *Scrawny to Brawny: The Complete Guide to Building Muscle the Natural Way*, Rodale Inc., 2005, hereby incorporated by reference in its entirety, state that it takes about seven to fourteen days for the body's immune system to rebuild muscle fibers broken down during exercise. More importantly, during this process these muscle fibers are rebuilt even stronger than the fibers that existed before exercise began.

The present invention further provides convenient scheduling and personal training in a private setting, utilizes isometric contractions on solid state fitness equipment, and analyzes the exerciser's medical information so that the proper amount of muscle tissue recovery and development time can be determined for each exerciser at every appointment. By providing for a mandatory recovery time between exercise appointments and custom-tailoring, the length of the recovery time is adjusted to the physiological needs of the individual. As such, the systems and methods of the present invention ameliorate the increasing problem of exercise-related injuries.

In addition, by utilizing the isometric contraction model, also known as the maximum static contraction method, as a primary exercise regimen, this invention provides a convenient and effective exercise program for its participants. Numerous authors in both fitness and medical literature have documented the effectiveness of the maximum static contraction method of strength and fitness training This model has convincingly been shown to improve muscle metabolic efficiency and optimize energy utilization, as well as minimize the inevitable muscle mass loss associated with the normal aging process. Muscle mass maintenance can then indirectly prevent weight gain by maintaining the higher basal metabolic rate associated with this increased muscle mass. The key is a combination of optimal muscle effort to stimulate growth and development while allowing adequate rest for complete recovery. The importance of recovery is emphasized by M. Doug McGuff, MD, *Maximize Your Training*, Brzycki (ed.), McGraw-Hill, hereby incorporated by reference in its entirety, who states "In general, we have found that 7 days of recovery is long enough for most, and is not too long for anyone." Furthermore, this invention's exercise program also only requires a minimal amount of the exerciser's time, which is likely to increase the exerciser's long-term commitment to the program.

Thus, prior to this invention's exercise program and administrative system, there was no science-based, physical fitness system available that combines ultimate safety with convenience and sustainability. This invention addresses each and every aspect of strength development from injury reduction and/or elimination, to the retention of exercisers' interest as they progress in the program and their need for physical fitness grows more important year by year.

The present invention, seeks to change the way that individuals get in shape by providing a new method of strength training that only requires a minimal amount of time and virtually no sweat from its participants. Moreover, this invention challenges many of the fitness industry's current trends by creating a sustainable strength training program that appeals to a much broader population base while promising to reduce injury risk factors. This program refutes the premise that injury is implicit to sport while making advances in addressing an important issue in sports medicine—increasing obesity and diminishing fitness in an aging society. This invention also aims to teach maturing adults that while a working heart is essential to life, skeletal muscle strength is also needed to enjoy it. Consequently, the systems and methods in accordance with the present invention target individuals interested in improving their health and fitness, but unsatisfied with existing exercise programs by providing a sustainable, time-efficient, and safety-conscious alternative to conventional fitness programs.

To achieve the aforementioned goals, the systems and methods of the present invention utilize a relatively new muscle-building concept known as the "isometric contraction" method, or the maximum static contraction method, to help exercisers build skeletal muscle strength. Unlike conventional programs that implement highly repetitive resistance training (using free weights) programs, this invention's isometric contraction methodology uses relatively infrequent maximum muscle contractions to build skeletal muscles. Furthermore, this isometric contraction exercise regimen is followed by a new rest and recovery technique that is monitored by the invention's custom software and central data processing system.

Exercisers in this program perform any combination of at least four different isometric contraction exercises: bench presses, leg presses, bent rows, and deadlifts. All of these exercises are performed on solid-state exercise equipment designed specifically for this business method invention. For the purposes of this invention, "solid-state" equipment means exercise equipment that has few or no moving parts. In other words, unlike traditional exercise equipment, solid-state equipment does not require an exerciser to lift blocks of weights up and down. Rather, exercisers in accordance with the present invention create pressure on the equipment while either sitting or standing. As the pressure increases, the exerciser must hold the position as long as possible. The exerciser releases the equipment when their muscles can no longer withstand the pressure. After the equipment is released, the final force exerted by the exerciser is determined and used as a basis for future exercises.

One of the advantages of the present invention is use of the principle of placing extreme stress on a particular fully contracted muscle group in order to make the muscle group stronger when it regenerates. Therefore, the momentary muscle failure experienced by an exerciser's experience in this static contraction program is, in fact, just a means of stimulating the exerciser's muscles to develop and grow.

Optimal muscle development is central to the purpose of the program, improved strength and fitness for its exercisers. This program takes as its premise the principle that muscle mass at rest burns more calories than fat or non-muscle tissue. In fact, if one gains ten pounds of muscle, this extra muscle will burn the caloric equivalent of running five miles a day, seven days a week. Thus, by participating in this muscle building program, exercisers will essentially be able to concomitantly increase both their muscle mass and their metabolic rate.

However, in order to achieve optimal muscle development, the systems and methods of the present invention also utilize strategic rest periods between exerciser's exercise appointments. In order to attain the optimal rest period, this program relies on its custom software programs to analyze each exerciser's performance and determine how much recovery time is needed. An important aspect of the present invention is optimization of the rest interval between exercises in order to allow muscles to properly rehabilitate without the threat of injury.

Taking into account an average rest period, exercisers enrolled in a program in accordance with the present invention need only visit an enterprise office once every other week for a few minutes in order to comply with the inventive regimen. Furthermore, exercisers typically do not even have to change into exercise clothing in order to engage in the program because the exercises in accordance with the present invention typically do not cause a person to break a sweat. Thus, the inventive program requires a substantially smaller time commitment than many known exercise programs. Therefore, a large number of people who were unable to stay committed to such known fitness programs will benefit from the exercise regimens of the present invention.

In addition to identifying the optimum rest period for each exerciser, this invention's unique equipment, software, and central data system are also components of an overall administrative system. For instance, the equipment used in the present invention accurately collect exercise results. Such results can be viewed on a graphical display during the exercise appointment and/or any time after the appointment via an enterprise website. This data is also used to identify the optimum exercise regimen for the exerciser's next exercise appointment, including maximum force and the optimum amount of time the exerciser should wait before the next exercise session.

In addition to facilitating appointment scheduling, the centralized processing system offered in embodiments of the present invention also fully supports internal physiological research, administration of the enterprise, electronic billing and merchant banking, and further allows a plurality of exercisers in disparate locations (e.g., across town, state, or country) to have their medical information encrypted and treated confidentially.

One aspect of the invention provides a method of facilitating an isometric contraction exercise regimen for a subject. The method comprises developing one or more exercise constraints as a function of the medical health information of the subject. Next, the subject performs a plurality of isometric contraction exercises using exercise equipment in the presence of a fitness trainer thereby producing a set of exercise results. The exercise equipment has one or more strain gauges in order to impose or monitor exercise constraints in the one or more exercise constraints. A mandatory recovery period is imposed for the subject after performing the plurality of isometric contraction exercises during which time the subject does not perform isometric contraction exercises. The exercises interspersed between mandatory recovery periods are repeated using a new set of one or more exercise constraints that are refined based upon previous exercise results. In preferred embodiments, the fitness trainer is not assigned to any other subjects when the subject is performing exercises supervised by the fitness trainer.

Still another aspect of the invention provides a computer program product for use in conjunction with a computer system. The computer program product comprises a computer readable storage medium and a computer program mechanism embedded therein. The computer program mechanism comprises instructions for receiving medical health information of a subject enrolled in an isometric contraction exercise regimen. The computer program mechanism further comprises instructions for developing one or more exercise constraints as a function of the medical health information of the subject. The computer program mechanism further comprises instructions for receiving an exercise result from a plurality of isometric contraction exercises that were performed by the subject using exercise equipment in the presence of a fitness trainer. The exercise equipment has a strain gauge in order to impose or monitor exercise constraints in the one or more exercise constraints. Data from the strain gauge is found in the exercise result. The computer program mechanism further comprises instructions for creating a mandatory recovery period for the subject after the subject has performed the exercises. The exerciser does not form isometric contraction exercises during this recovery period. The computer program mechanism further comprises instructions for repeating the aforementioned instructions using a new set of one or more exercise constraints that were refined based upon previous exercise results.

Yet another aspect of the invention provides a computer system for facilitating an isometric contraction exercise regimen for a subject. The computer system comprises a central processing unit and a memory, coupled to the central processing unit. The memory stores a computer program mechanism. The computer program mechanism comprises instructions for receiving medical health information of a subject enrolled in an isometric contraction exercise regimen. The computer program mechanism further comprises instructions for developing one or more exercise constraints as a function of the medical health information of the subject. The computer program mechanism further comprises instructions for receiving an exercise result from a plurality of isometric contraction exercises that were performed by the subject using exercise equipment in the presence of a fitness trainer. The exercise equipment has a strain gauge in order to impose or monitor exercise constraints in the one or more exercise constraints. The data from the strain gauge is found in the exercise result. The computer program mechanism further comprises instructions for creating a mandatory recovery period for the subject during which time the subject does not perform isometric contraction exercises. The computer program mechanism further comprises instructions for repeating the instructions for receiving, and the instructions for creating using a new set of one or more exercise constraints that were refined based upon the exercise results of a previous instance of the instructions for receiving.

Still another aspect of the invention provides an exercise apparatus for facilitating an isometric contraction exercise regimen for a subject. The exercise apparatus comprises a casing, a strain gauge housed within the casing, a central processing unit housed within the casing, and a memory housed within the casing, coupled to the central processing unit, the memory storing a computer program mechanism. The computer program mechanism comprises instructions for receiving one or more exercise constraints. The one or more exercise constraints are determined as a function of the medical health information of the subject by a remote computer. The computer program mechanism further comprises instructions for computing an exercise result from an isometric contraction exercise that was performed by the subject using the exercise apparatus in the presence of a fitness trainer. The exercise apparatus uses the strain gauge in order to impose an exercise constraint in the one or more exercise constraints. The computer program mechanism further comprises instructions for sending the exercise result to the remote computer as well as instructions for repeating the aforementioned instructions using a new set of one or more exercise constraints such that the set of one or more exercise constraints are refined based upon the exercise results of a previous instance of the instructions for computing. Furthermore, the instructions for repeating are performed after a mandatory recovery period for the subject that was determined by the exercise result of a previous instance of the instructions for computing.

BRIEF DESCRIPTION OF THE DIAGRAMS AND DRAWINGS

The present invention has many advantages and features that will be more readily apparent from the diagrams, drawings, descriptions, and claims that follow.

Figure 1:
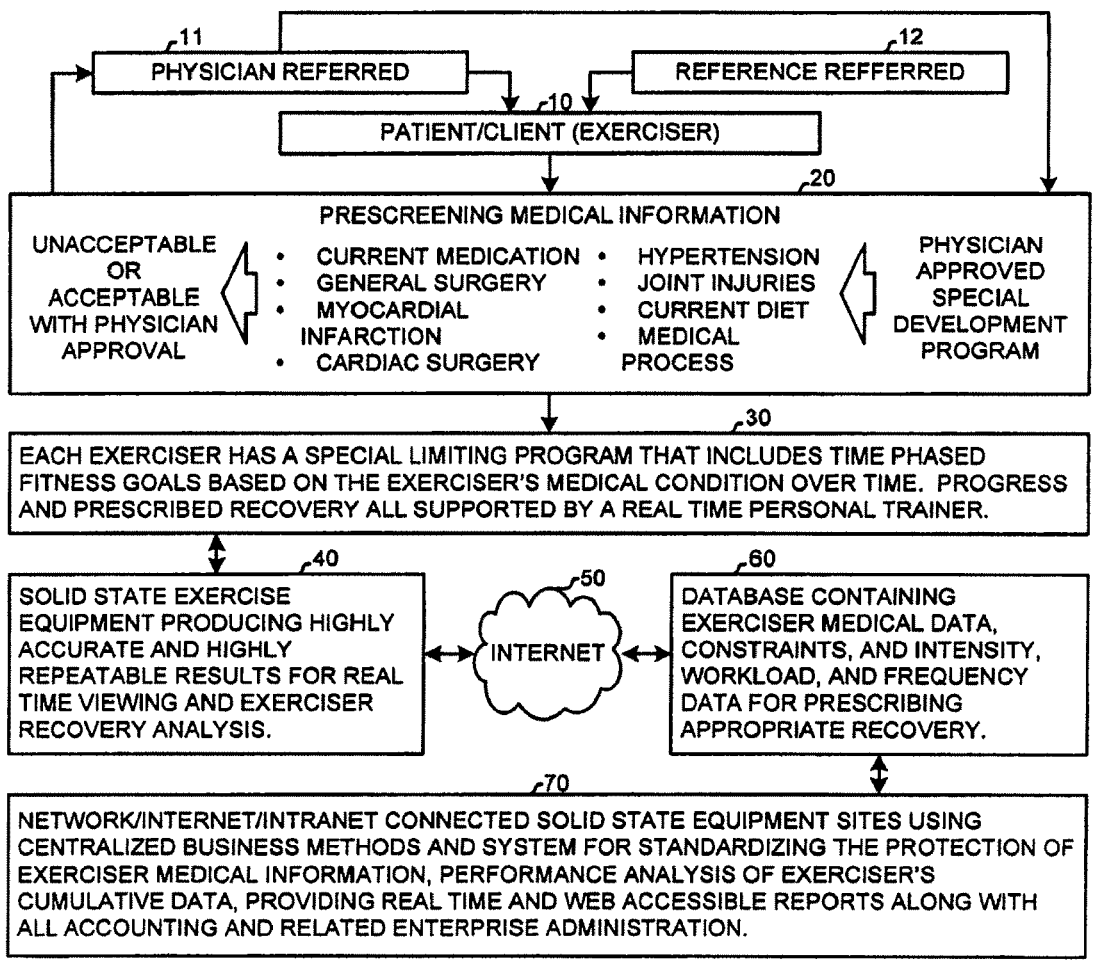
FIG. 1 illustrates a method for providing exercisers with improved health and fitness through increased muscle strength that is achieved without the risk of injury in accordance with an embodiment of the present invention.
Figure 5:
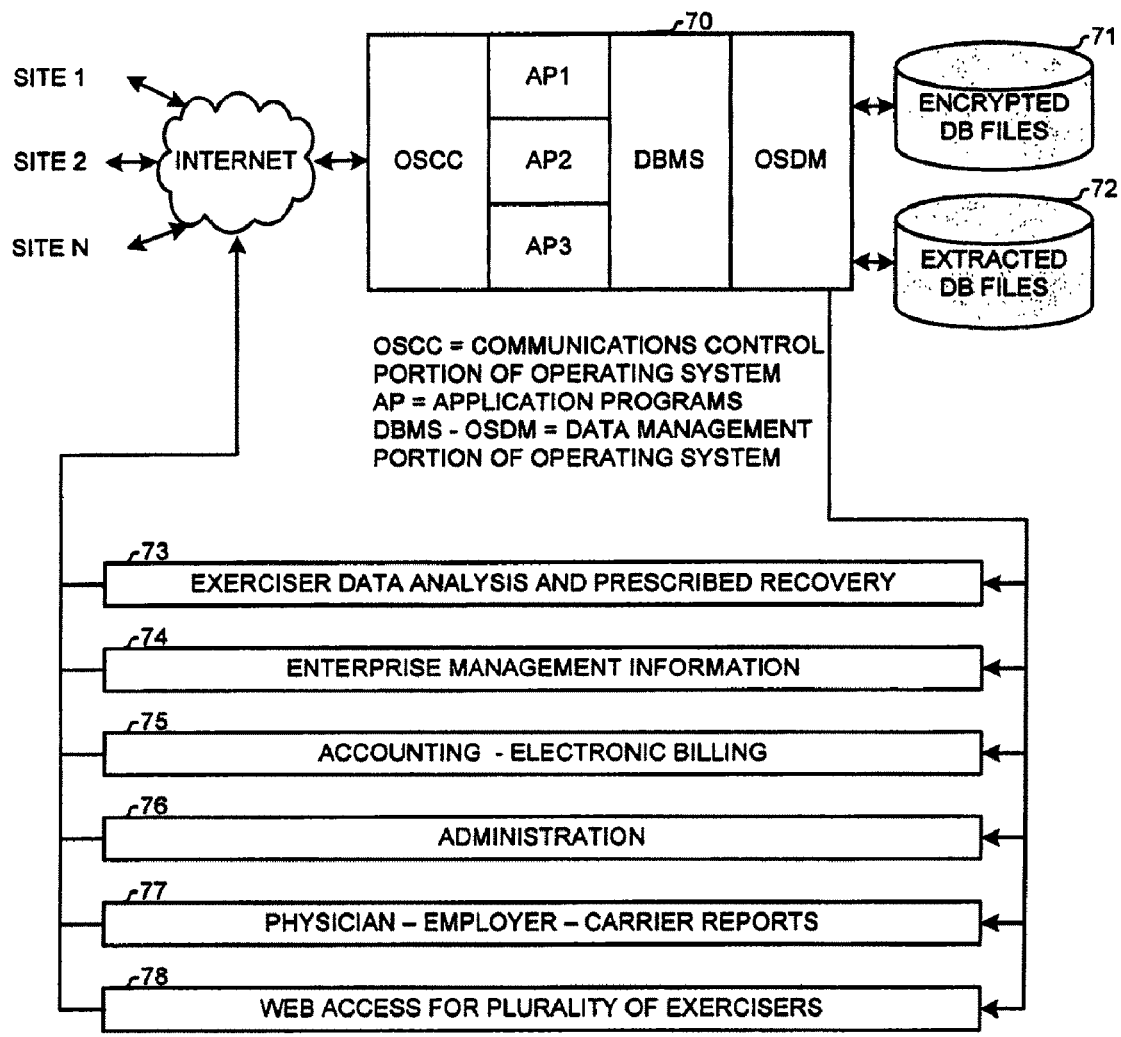
Figure 6A:
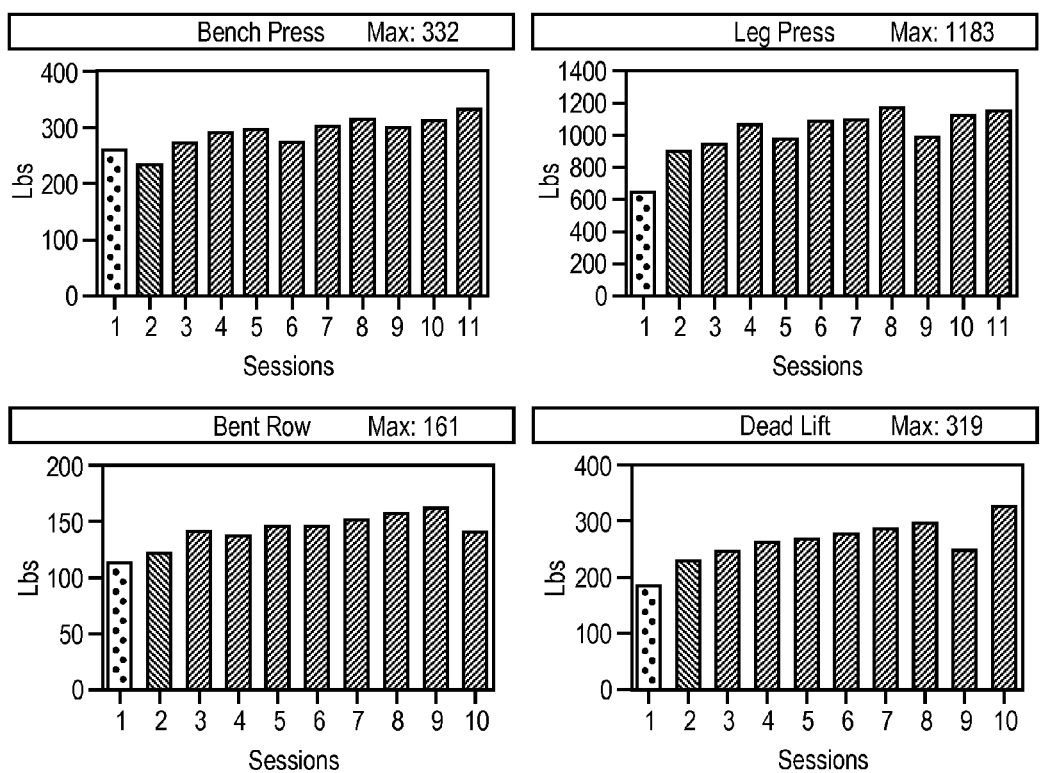
Figure 6B:
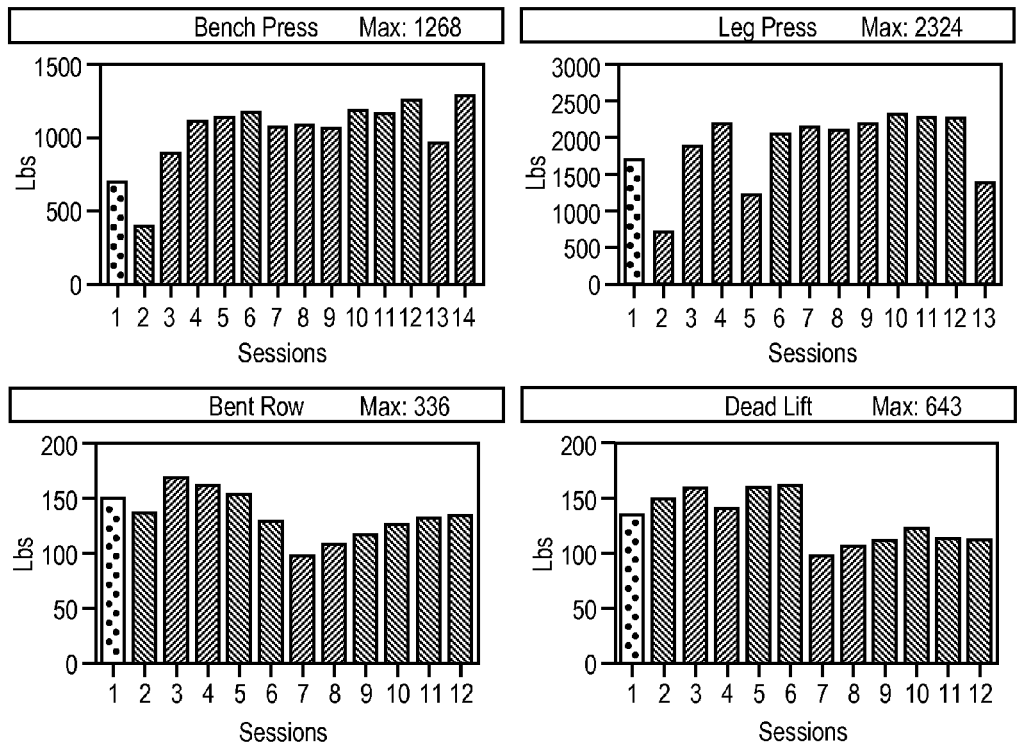
Figure 6C:
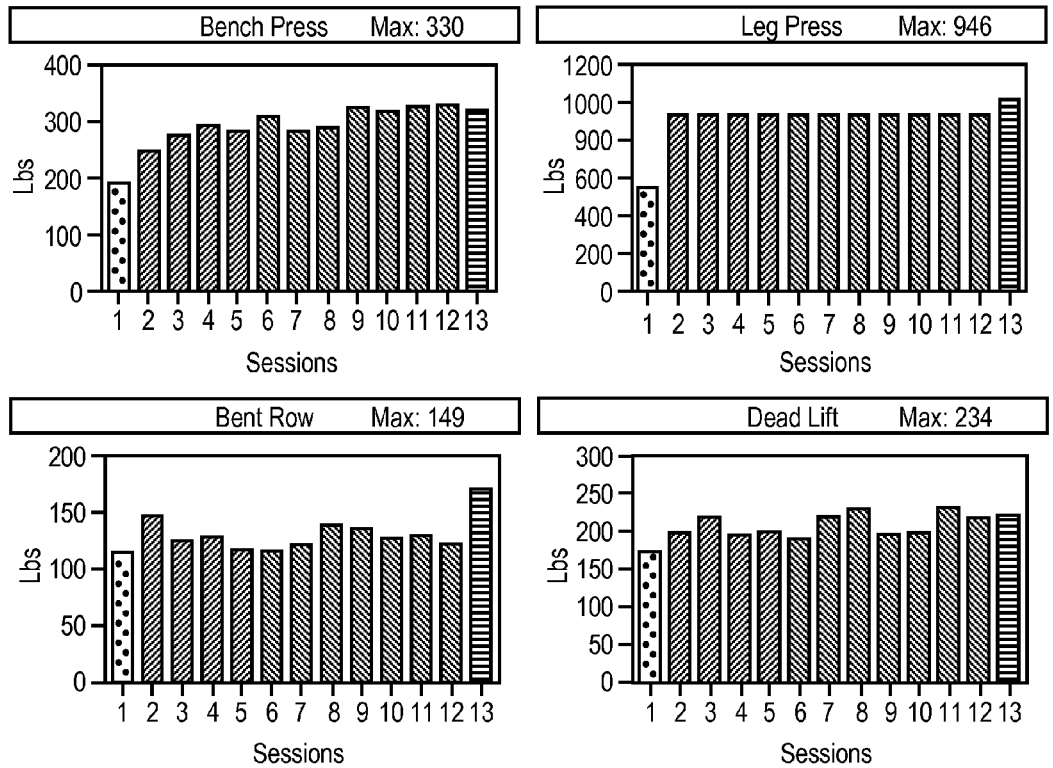
Figure 6E:
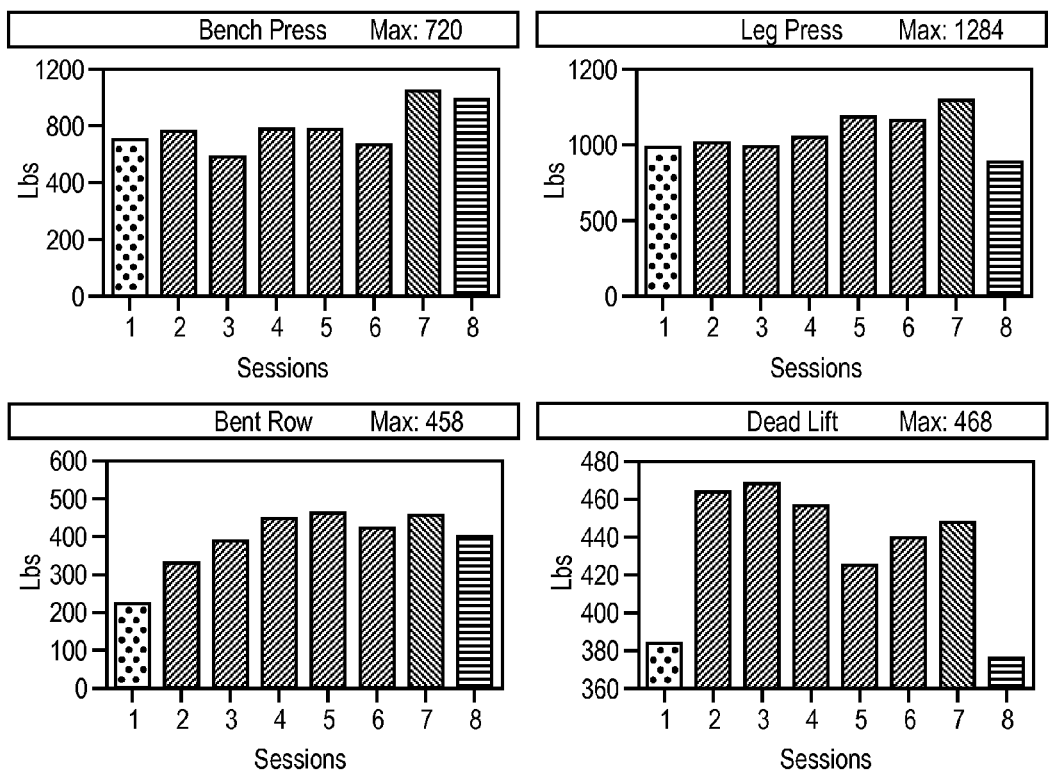
Figure 6F:
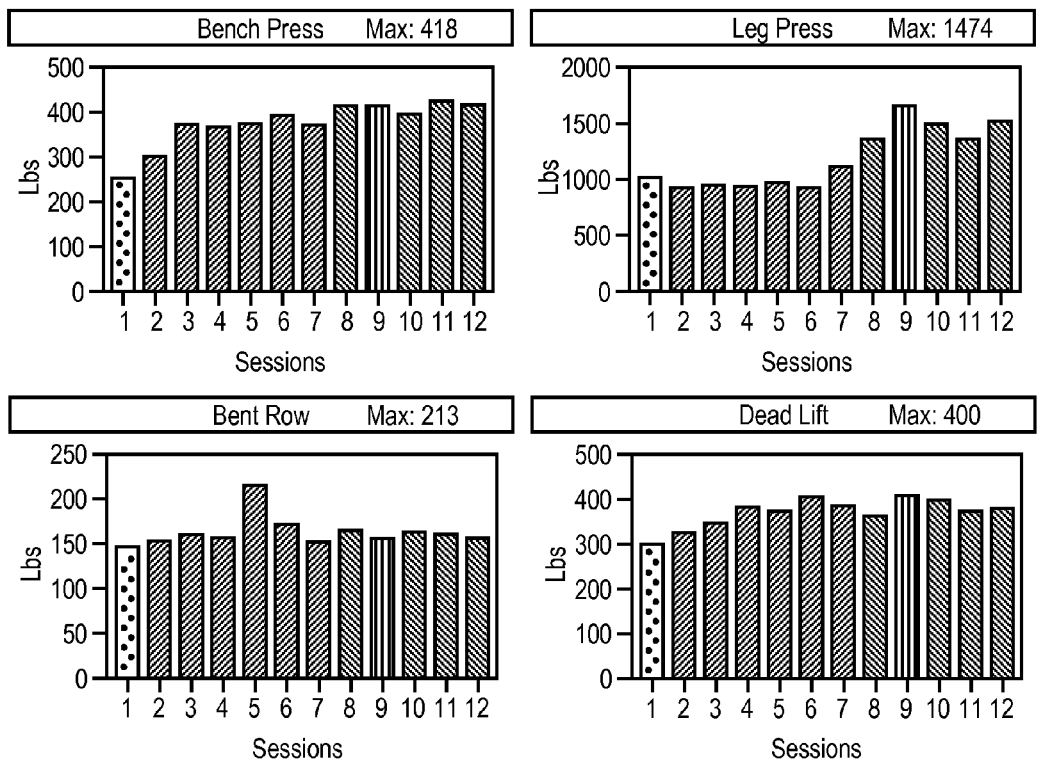
Figure 6G:
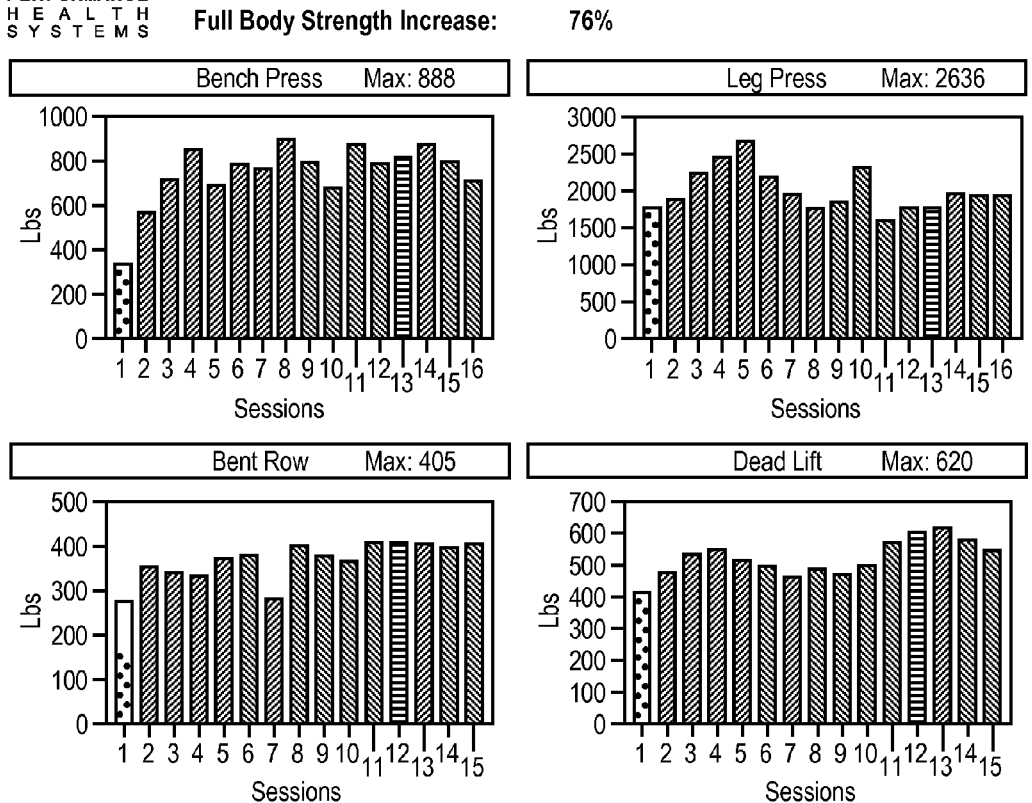
Figure 6H:
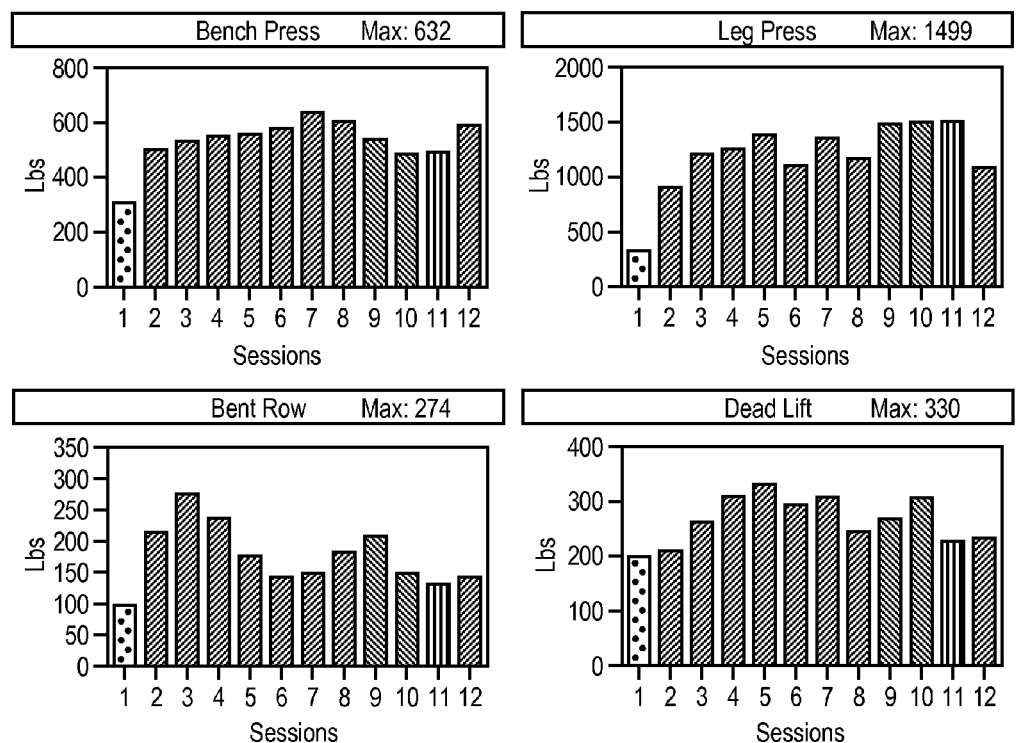
Figure 6I:
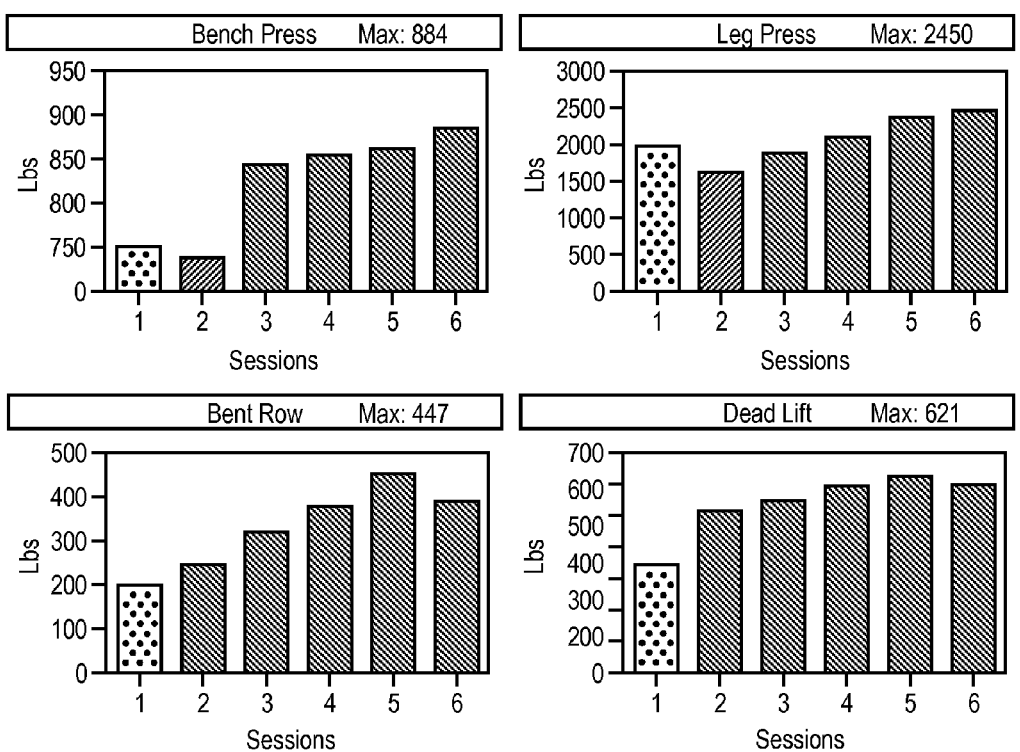
Figure 6J:
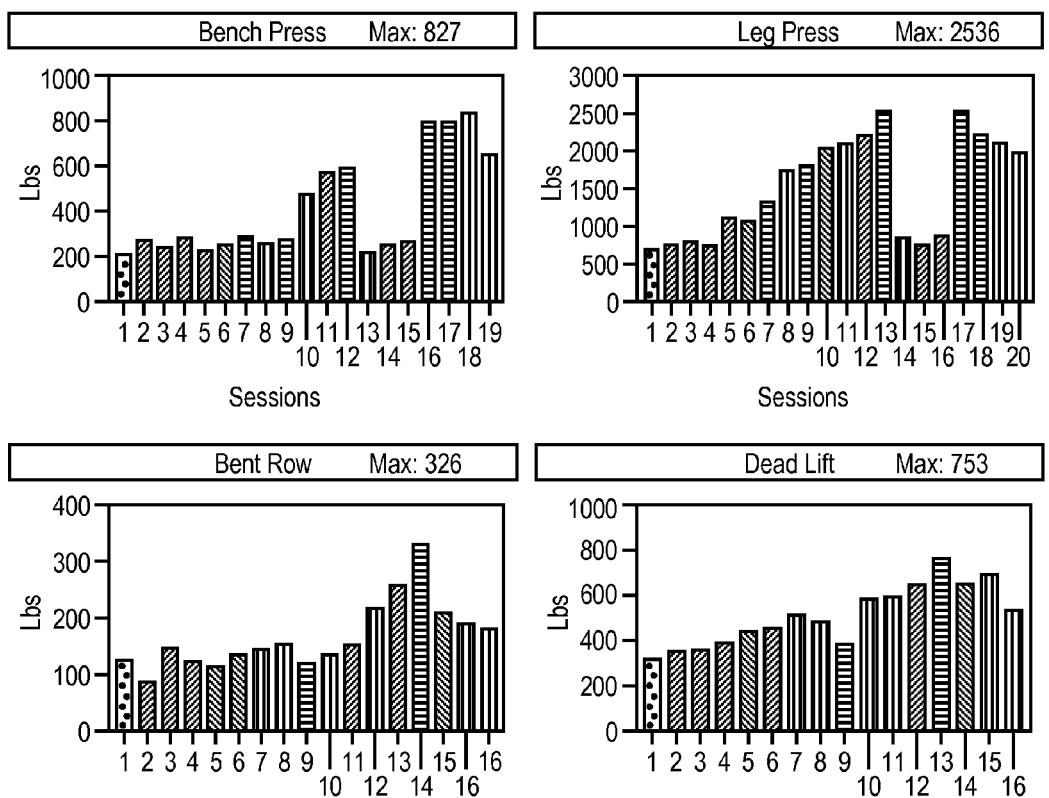

FIG. 5 is a diagram that shows a centralized business information processing and business administration system, providing medical information privacy to exercisers, progress information to exercisers, enterprise information, accounting, and administrative support from the network/Internet/Intranet connected facility shown in FIG. 1, while also providing appropriate exerciser information to physicians, employers, and insurance carriers.

FIGS. 6A-6J illustrate exercise results for individual exercisers that have used the systems and methods of the present invention.

DETAILED DESCRIPTION

Embodiments of the present invention are explained in the paragraphs that follow. FIG. 1 illustrates novel systems and methods for providing a safer, more sustainable fitness and strength building program for exercisers 10. In this new exercise program an exerciser's health risk factors are determined and then a unique fitness regimen 30 is fashioned for the exerciser 10 based on the exerciser's current state of health. Each individualized exercise regimen 30 utilizes custom-designed, solid-state exercise equipment 40 designed to reduce exercise related injuries.

As shown in FIG. 1, in some embodiments prospective exercisers 10 may be referred to this exercise program by a physician 11 or any other recommender 12. Then, as shown in detail in FIG. 2, potential exercisers 10 undergo an initial health risk prescreening process 21 before beginning their exercise regimen 30. In some embodiments, prescreening process 21 is conducted with input from the exerciser's physician 11.

Figure 2:
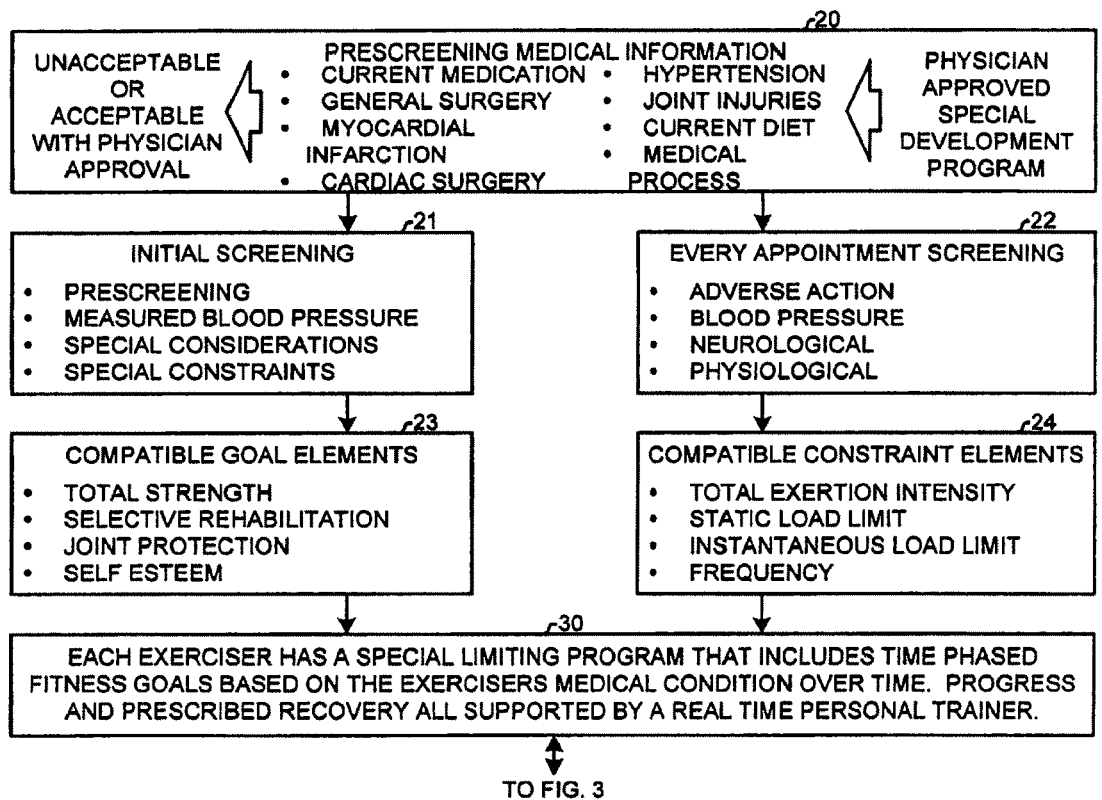
FIG. 2 is a diagram showing a physician-assisted process for setting exercise constraints and goals, where collected medical information dictates, allowing all acceptable exercisers to utilize the system, each with their own exercise program and prescribed recovery in accordance with an embodiment of the present invention.

As summarized in FIG. 2, during the initial screening process 21 each exerciser 10 describes any previous injuries to his or her arms, legs and spine, any previous surgery, any previous cardiac difficulties, e.g. arrhythmias (irregular heartbeat), myocardial infarction (heart attack), previous cardiac surgery or other problems, any previously diagnosis or treatment for hypertension, any medication currently being taken, any current special diet, any nutritional supplements/health food products currently being taken, any unexpected or expected weight changes in the last six months, any sustained injuries while participating in other exercise programs, or any unusual family medical history. Taken together, the exerciser's responses to the aforementioned questions is hereinafter referred to as "prescreening medical information" 20. Furthermore, it will be appreciated that the aforementioned questions are merely exemplary of a broad range of questions that could be asked. Furthermore, not all the aforementioned questions are required in order to obtain a complete set of prescreening medical information 20. Upon completion of this prescreening process 21 and only when needed, some exercisers 10 may also be referred to a physician who can determine what constraints are medically necessary to create a safe and effective exercise program.

As shown in FIG. 2, prescreening medical information 20 and any necessary physician's advice is then used to formulate an individually-tailored exercise regimen 30 for each exerciser 10 that takes into account their physical limitations and/or health risk factors. A set of exerciser-specific exercise limits, hereinafter referred to as exercise "constraint elements" 24, referred to herein also as "exercise constraints," are created in this process. Fitness "goal elements" 23 that are compatible with his or her pre-determined constraint elements 24 are also created in this process. In some embodiments, the exerciser's constraint elements 24 and goal elements 23 are transmitted via a network to a central data processing system 70 (see, e.g., FIG. 5). In some embodiments, this transmission is encrypted.

Referring back to FIG. 2, in some embodiments, each exerciser 10 is also screened on an appointment by appointment basis 22 (also referred to herein as "every appointment screening"). In the optional appointment by appointment screening process 22, each exerciser 10 optionally watches an electronic presentation of certain pertinent health issues prior to exercise participation. In some embodiments, exerciser 10 also answers specific questions during this process, such as: (i) have you sustained any new injuries to your arms, legs, or spine that can impair your ability to engage in the exercise program; (ii) have you experienced any new or different medical problems, including light-headedness or dizziness, that can impair your ability to engage in the exercise program, and (iii) do you have any reason to believe that your blood pressure may have become elevated since your last reliable check, e.g. pounding of your heart, headaches, etc.? Response to question (iii) may also be used to determine whether the exerciser's blood pressure needs be taken before exercising. One embodiment of the present invention includes the use of an on-site, automated, clinical quality blood pressure measuring machine to measure the exerciser's blood pressure that is electronically connected to the processing of the exerciser's private medical data.

In some embodiments, each exerciser 10 uses a personal access code to answer specific health questions that are displayed to the exerciser on an electronic display to ensure that the appointment by appointment screening process is completed. Furthermore, as a safeguard, an electronically controlled system also can prevent an exerciser 10 from exercising until all of these questions are answered. In some cases, if any medical problem surfaces during the exerciser's participation in the program, the exerciser may also need to re-enter the prescreening process 21 and provide additional medical information and specific medical evaluations again.

In some embodiments, both the initial prescreening 21 and appointment by appointment screening 22 have injury prevention as their primary objective. As a result, in such embodiments, the exerciser's fitness goals and medical constraints dictate in large measure the characteristics of the customized exercise program developed by the present invention's administrative system.

In the present invention, fitness trainers are present with the exerciser 10 during the exercise regimen. As will be disclosed below, fitness trainers can perform several functions in this program.

Referring to FIG. 2, in some embodiments, the results of the initial prescreening 21 and/or the appointment by appointment screening process 22 are presented to the personal trainer 30 and exerciser 10 before the exerciser 10 begins a new exercise session. It may also be the personal trainer's 30 job to explain to each exerciser 10 the advantages of this program's technology, equipment, and method of strength training as well as highlight how the present invention departs from other typical fitness programs that the exerciser 10 may have used previously. The fitness trainer may also assist exercisers 10 and prevent them from inadvertently misunderstanding what they are doing and why, which can result in the exerciser 10 realizing a very high value in this program.

In some embodiments of the present invention, exerciser 10 and the associated personal fitness trainer are separated from other exercisers 10 or environmental distractions. For example, they may be situated in a separate cubicle or possibly even in a private room. Such an environment enables the exerciser 10 to be freer to ask questions and conduct exercise training or testing. Providing a real-time personal training regimen 30 in a private setting can also eliminate many of the problems exercisers 10 currently have with the typical fitness industry programs because of the continuous expert oversight/motivation available to the exerciser 10 and the elimination of the social/psychological deterrents of a "gym" or "fitness center" atmosphere.

Figure 4:
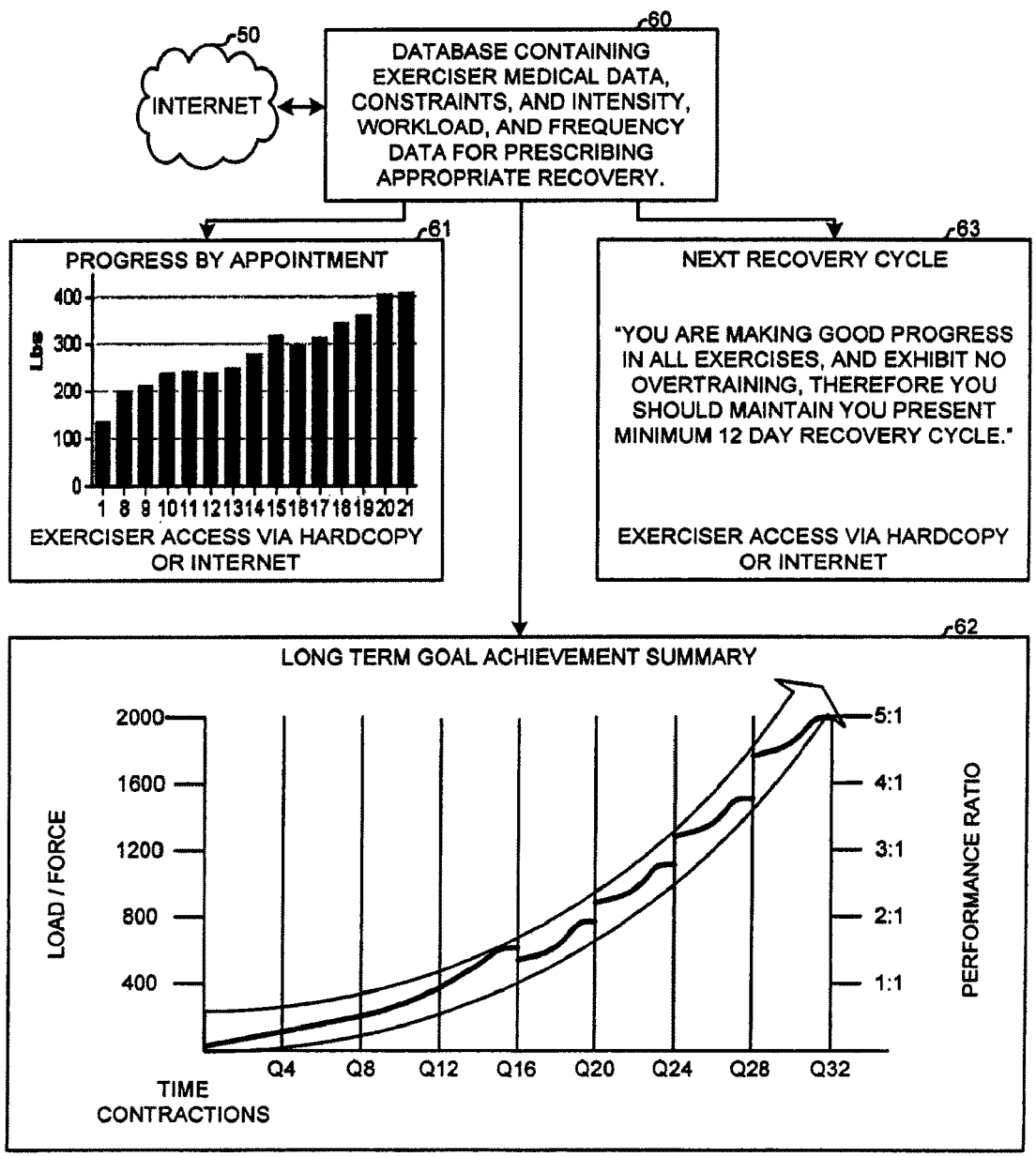
FIG. 4 is a diagram showing a database processing of exerciser medical data constraints, present exercise intensity, load/force, time, frequency and long term goal achievement, as well as the output from recovery specific algorithms, using the medical constraints as shown in FIG. 2 and current exercise data as shown in FIG. 3.

Referring to FIG. 4, in order to ensure the safety of this exercise program, many moving parts have been removed from exercise equipment used in the present invention. For example, unlike traditional fitness equipment that is comprised of heavy metal weights, pulleys, cables, springs, levers, chains, etc., all of which are hazards for exercisers 10 using such equipment 40, equipment in accordance with the present invention utilizes strain gauges 42 not weights in its structure, and does not have any moving parts that can fall and injure an exerciser 10. Removing the moving parts from this equipment also prevents exercisers from having to adjust the machines without proper instruction, which can often lead to machine misuse, an improper exercise experience, or even injury.

Figure 3:
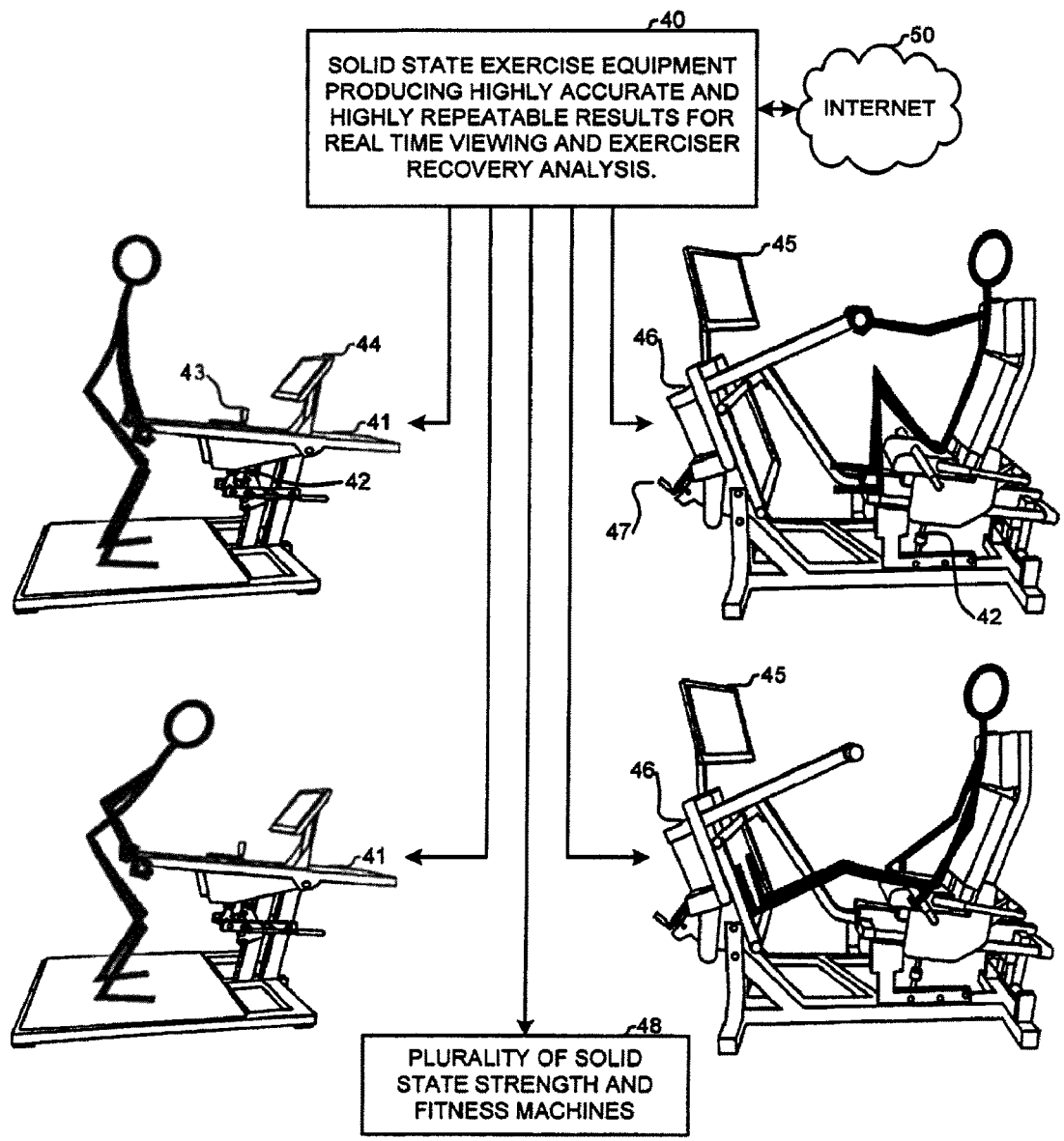
FIG. 3 is a diagram that shows a plurality of solid state exercise equipment sets for collection of individual exerciser data, and the real time display of strength training/testing results in accordance with an embodiment of the present invention.

In some embodiments of the present invention, exercisers 10 use custom designed, solid state fitness equipment 40, referred herein also as an "exercise apparatus," to exercise. FIG. 3 illustrates several different embodiments of this equipment 41, 46 and also depicts a person performing four of the exercises—dead lift, bent row, bench press, and leg press—that may be performed on this equipment. Advantageously, the solid state fitness equipment 40 of the present invention enables a person to perform these exercises by taking the relevant muscle groups to failure while they are in a fully contracted state. Because fully contracted muscle strength is maximized, in preferred embodiments of the present invention solid state fitness equipment 40 withstands 5,000 pounds of exerciser applied load. Further, since no movement is required during the exercises of the present invention, solid state fitness equipment 40 must be configured such that exerciser 10 is in a comfortable position at all times in order to maximize the applied loads. Since solid state fitness equipment 40 are no movement machines, they are configured to accommodate the anatomical differences among exercisers 10. For this reason, a health advisor is present for the exercises conducted in accordance with the present invention to make adjustments apart from any action taken by exerciser 10.

Equipment 40 used in the systems and methods of the present invention can have any combination of the following features. One such feature is a strain gauge. In some embodiments, this strain gauge is very accurate and makes equipment 40 easily adjustable for different exerciser body types. In some embodiments, this strain gauge is enclosed by adjuster screws 43 for safety. In some embodiments, equipment 40 has the feature of operating without any moving components. In some embodiments, equipment 40 has an electronic display that allows the exerciser 10 and their personal trainer to see, in real time, the exerciser's incremental exercise results. In some embodiments, equipment 40 has the feature of being specially designed to produce highly accurate and reproducible exercise results. In some embodiments, equipment 40 has the feature of being able to produce fitness training/testing results that are approximately ten times more accurate than the current fitness industry equipment. In these embodiments, such results are used to produce each exerciser's individualized exercise regimen 30 and to calculate customized required recovery periods 63 (e.g., FIG. 4).

In some embodiments, both the actual manner in which an exerciser 10 exerts force on equipment 40 during an exercise session and the manner in which these forces are measured, processed and combined with user-specific medical information, produce a result not previously sought by any health and fitness provider and one that is not currently available using traditional fitness equipment or fitness concepts.

In some embodiments, an exerciser 10 begins the exercise program by making an appointment at the enterprise site. In some embodiments, this appointment is conducted in a professional manner and resembles a doctor's appointment in its formality. In some embodiments, the value of the exercise program is discussed with the potential exerciser 10.

If the exerciser 10 finds the information given in the initial appointment satisfactory, they may then choose to sign up for the program. In some embodiments, the exerciser 10 provides certain required general information, which may include health status, prescreening medical information 20, and identification information. In addition to providing health and contact information, the exerciser 10 may also give appropriate billing information for the centralized electronic billing program 75 (FIG. 5). In some cases, exerciser 10 may also need to get a physician's approval to sign up for the program. The first appointment is approximately thirty minutes long in some embodiments. Exerciser 10 is then assigned an administrative identity. In some embodiments, this identity is encoded on an identification card capable of interfacing with the present invention's administrative system.

In some embodiments, a fitness trainer begins to provide exerciser 10 with further instructions and information about the program, including information about the exercise types, equipment 40, data collection methods and recovery periods 63 that comprise this program once the initial appointment is complete. In other embodiments, exerciser 10 schedules a second appointment where he or she will perform the full exercise regimen 30 in the presence of a fitness trainer. In some embodiments, this second appointment is twenty minutes or less.

The present invention's exercise regimen 30 utilizes exercises based on the isometric contraction method of exercise. The exercises performed in the present invention are heretofore referred to as "isometric contraction exercises." An isometric contraction exercise is an exercise in which an exerciser positions one or more muscle groups in a fully contracted state and creates an increasing amount of force while the one or more muscle groups are kept in the fully contracted state until the one or more muscle groups fail to create any more force (muscle failure). As such, isometric contraction exercises cause a muscle to exert force but do not cause the muscle to change in length. Isometric contraction exercises require maximum muscle contraction and require specific muscle groups to create increasing amounts of force until the muscle groups fail to create anymore force.

In some embodiments, regimen 30 includes several different types of isometric contraction exercises. In some embodiments, exercisers 10 initially engage in less complex isometric isometric contraction exercises, and then more demanding multi-isometric contraction exercises as the exercise regimen progresses.

In some embodiments, the isometric contraction exercises work all major muscle groups thereby achieving a full body workout. In some embodiments, exercisers 10 perform four isometric contraction exercises: bench presses, leg presses, bent rows, and dead lifts as seen in FIG. 3. In each of these isometric contraction exercises, the relevant muscle groups are maintained in the fully contracted state while creating increasing amounts of force until muscle failure is achieved. In some cases, all of these exercises are performed on solid-state exercise equipment 40 designed specifically to allow the exerciser to fully contract the relevant muscle groups while creating increasing amounts of force with the fully contracted muscle groups.

A description of isometric contraction exercises in accordance with some embodiments of the present invention will now be described. A goal of each of these isometric contraction exercises is to achieve the maximum level of muscle fiber involvement. Without intending to be limited to any particular theory, the isometric contraction exercises are based on the observations that (i) muscle fibers contract by reducing their length; (ii) a muscle is in the fully contracted (peak position) when all the fibers of the muscle are contracted simultaneously; and (iii) to get all the fibers of a muscle to contract at the same time, a load intense enough to activate all of the muscle's fibers needs to be imposed. The four basic isometric contraction exercises described here are improved versions of traditional compound, multi joint exercises.

Bench press isometric contraction exercise. The exerciser's proper position for the bench press isometric contraction exercise of the present invention requires the exerciser to be in a sitting position, with arms positioned in a horizontal plane passing through the shoulder joints, and holding about 2-3 inches short of where the arms are fully extended, the strongest part of the exercise. In this position, an exerciser can go to failure using one hundred percent of muscle fiber in the triceps, deltoids, and the pectorals. The exercise begins and ends in this position and there is only nominal movement due to compression of connective tissues within the body as well as the pad which sits behind the exerciser.

Leg press isometric contraction exercise. The exerciser's proper position for the leg press isometric contraction exercise of the present invention requires the exerciser to be seated upright and in no way semi supine. The exerciser is positioned in a seat with a high back and hand grips which is held to avoid riding up in the seat when performing the exercise. The upright positioning is dictated by the need to allow women in street clothes, who may possibly be wearing a skirt to avoid having her legs in an upright position at any time. When the exercise is performed the exerciser's legs are 4-6 inches from the position where the legs would otherwise be fully extended, the strongest part of the exercise. In this range an exerciser can go to failure using one hundred percent of muscle fiber in the quadriceps and the gluteus maxims. The exercise begins and ends in this position and there is only nominal movement due to compression of connective tissues within the body as well as the pad which sits behind the exerciser.

Bent row isometric contraction exercise. The exerciser's proper position for the bent row isometric contraction exercise of the present invention requires the exerciser to stand with legs close to the bar to be lifted. The bar is positioned 2-3 inches above the exerciser's knee. The exerciser performing the bent row isometric contraction exercise must keep the bar almost touching the bottom of the rib cage as the exerciser is in a bent knee stance and has the upper body tilted forward at a 45 degree angle. In this range, an exerciser can go to failure using one hundred percent of muscle fiber in the biceps brachia, and the latissimus dorsi. The exercise begins and ends in this position and there is only nominal movement due to compression of connective tissues within the body.

Deadlift isometric contraction exercise. The exerciser's proper position for the deadlift isometric contraction exercise of the present invention requires the exerciser to stand close to the deadlift bar, where the bar is located 2-3 inches above the exerciser's knee, and at the top most position where the bar is laying against the thighs and is being gripped so that the load is taken by a pulling motion as the center of gravity is close to the body, this results in the exerciser having proper balance and contraction of almost every muscle on the back side of the body. In this position, an exerciser can go to failure using one hundred percent of the muscle fiber in the hamstrings, spinal erectors, trapezius, abdominals, calves, and forearms. The exercise begins and ends in this position and there is only nominal movement due to compression of connective tissues within the body.

In the present invention, exercisers 10 use their muscles to create a force resisted and measured by equipment 40. In some embodiments, strain gauges on exercise equipment 40 are utilized to measure the amount of force used in the isometric contraction exercise. In other embodiments, the strain gauges monitor the amount of force exerciser 10 is voluntarily creating. In some instances, exerciser 10 creates pressure while they are sitting or standing.

In some embodiments, exerciser 10 creates the increasing force as long as possible. The exerciser 10 releases equipment 40 when the exerciser's targeted muscle groups cannot withstand the pressure any longer. In some embodiments, after the exerciser 10 releases equipment 40, the present invention's computer systems and software are designed to measure the maximum force the exerciser 10 was able to create. The maximum force is an example of one form of "exercise result" in accordance with the present invention. In other embodiments, the number of repetitions the exerciser completes is an exercise result. In still other embodiments, the length of time that the exerciser created the force is an exercise result.

In some embodiments, exerciser 10 can view graphical displays of exercise results both during the exercise appointment and/or any time after the exercise appointment via the enterprise website 78 (FIG. 5). In some embodiments, this information is also be available on a display 45 that is attached to exercise equipment 40 as illustrated in FIG. 3. In addition, in some embodiments, each exerciser may visually see the incremental progress made on an appointment by appointment basis 61, and/or the progress made against long term goal elements 62 (FIG. 4). In some instances, the exerciser's exercise results are transferred via a network in an encrypted manner to a central data processing system 70. In one embodiment of the present invention, exercisers 10 initially build strength at a rapid rate, but then their strength gains are slowed down due to physical limitations which could include, but are not limited to, lack of progress in their bench press exercise progress or inability for their hands to handle the load that is put upon them. In such embodiments, the intensity of the exercise regimen 30 is slightly decreased. The intensity of the program is restored by concurrently (i) increasing the number of consecutive contractions and (ii) decreasing the amount of time allotted to complete such contractions. In some embodiments, an exerciser's regimen 30 is determined by first calculating a force number that is below their maximum isometric load/force. Then a determination is made as to how many times they can hit that load/force number. As the client progresses, higher contraction numbers are chosen and progress is monitored by looking at how many contractions can be achieved with the intended force in the shortest time. These values are then compared to previous performances with the same force applied. Progress in such an embodiment is graphically illustrated in FIG. 4 as graph 62.

Advantageously, exerciser 10 does not need to change clothing to perform the present invention's exercises, and may in fact perform them in any clothing. In some embodiments, exercisers 10 can arrive comfortably in their street clothing, and leave a few minutes later looking like they did when they arrived for their appointment. In some embodiments, a complete exercise appointment lasts twenty minutes or less, fifteen minutes or less, ten minutes or less, or even five minutes or less. After completing an exercise regimen 30, the exerciser 10 waits a specified amount of time, which allows the body to recover and then develop additional skeletal muscle, before completing another exercise regimen 30. This period of time where the exerciser performs no isometric contraction exercises is referred herein as the "recovery period" 63 (also referred to herein as the "recovery cycle"). In some embodiments, the exerciser 10 receives a hard copy print-out of the appropriate recovery period 63 or may access the recovery period 63 via the Internet. In some embodiments, this information may also be available on display 45 located on the exercise equipment 40 (FIG. 45).

In some embodiments, the recovery period is calculated based on previous exercise results and the exerciser's pre-screening medical information. In some embodiments, the recovery period is a function of an exerciser's exercise result and the results or experience trends of other exercisers that use the present invention's isometric contraction exercise regimen. In some instances, these other exercisers share one or more characteristics in common with the exerciser 10. Such characteristics may include health conditions, age, or gender.

Once the recovery period 63 is complete, the exerciser 10 returns to the equipment 40 to perform another set of exercises in the presence of a fitness trainer. Such activity is referred to as a "subsequent exercise appointment." In some embodiments, the type of exercises, the repetitions, the exerciser created force, or other variables are different in subsequent exercise appointments.

In some embodiments, data analysis 73 is performed once system 70 receives two or more exercise results. In some instances, the force created for any given exercise across multiple exercise appointments is evaluated together in order to determined changes in performance. As an example, the force created in a specific exercise type during one exercise appointment can be compared to the force created in an exercise of the same exercise type during another exercise appointment and the two results can be evaluated together for performance changes. In some embodiments, the results of the data analysis 73 are combined with any exercise constraints set by a physician in order to dictate changes in the exerciser's program details. Such changes include, but are not limited to, recovery period length 63, the amount of force created, the number of exercise repetitions, the type of exercises performed, the instantaneous load/force limit, the static load/force limit, and total exertion intensity.

In some embodiments, when an exerciser's incremental progress begins to slow, possibly from overtraining, more time can be added to the recovery period 63. In such instances, for example, exercise appointments can be scheduled every other week. In some embodiments, a lower demand is placed on the connective tissue but a similar type of momentary muscular failure is still achieved, and the exerciser 10 is able to continue their strength development. Furthermore, when an exerciser 10 begins to near their muscular genetic potential, meaning that they have developed muscles worked by the exercise regimens of the present invention to their fullest possible extent, maintenance of such a condition can require as little time as one to two appointments per month. As a result, some embodiments of the present invention are capable of meeting the needs of exercisers 10, in part because they will have gradually increasing long term goals that they can work toward and met over an extended period of time.

The present invention includes a central data processing system 70, also referred to as a "central system," that assists in the administration of the present invention's exercise program. Aspects of a central system in accordance with the present invention are illustrated in FIGS. 4 and 5.

In some embodiments, this central system assures one or more of the following: the privacy needed for medical information, a totally disciplined structure for all types of information collection, a consistent manner in which prescreening medical information is collected by appointment, and the general administration of the business, including, all reporting, accounting and electronic billing 75. In other embodiments, the present invention's central system 70 receives its data from a plurality of sites via a network 50 and subsequently processes, distributes, and stores, encrypted db files 71 and extracted database files 72 for future access and segmentation analysis.

In some embodiments, the present invention's communications control, application programs, database management system, and operating system data management reside within central system 70. Together these elements protect, process, store and distribute the information necessary for the operation of the exercise program.

In some embodiments of the present invention, 50, a plurality of exercise training sites can transmit exercisers' medical information and exercise data, including but not limited to exercise results, constraints, or goal elements, to a central data processing facility utilizing a Network/Internet/Intranet or wireless connection 50 while maintaining the privacy of each exerciser's confidential data in the process. In some embodiments, this data is encrypted while being transferred.

In some embodiments, exerciser specific analysis 73 is performed when this data reaches central data processing system 70. In other embodiments, this analysis 73 utilizes interactions between databases, proprietary algorithms, and standard statistical techniques commonly used in the medical industry. In addition, in some embodiments, the resulting output information includes exerciser progress by appointment 61, long term goal achievement 62, and next recovery period 63 instructions. In the present invention, the prescribed recovery period 63 dictates the amount of time before an exerciser can have his or her next exercise appointment.

The ability to transmit data from a plurality of sites via a network 50 may also allow the processing and storage of exercise data for each individual exerciser 10. In some embodiments, this data is processed and stored for each exercise an exerciser 10 performs during a training session. Furthermore, the embodiments having accurate and reproducible data collection methods are able to make and store reliable accurate data calculations. In some embodiments, the results of these data calculations 61, 62, and 63 are displayed so that each exerciser 10 can graphically see their own progress.

In some embodiments, both personal trainers and other interested parties are provided an exerciser's specific data and progress information. In addition, some embodiments also provide real time support for personal trainers. In some instances, the automation and centralization of data processing in the central server 70 precludes personal trainers from changing any data. In some embodiments, the central server' central processing functions assure that personal trainers are fully supported by software driven help functions that permit them to address any exercisers 10 needs correctly and consistently from a plurality of personal trainers, located across a distributed network.

In some embodiments, the central system 70 also performs the necessary accounting and billing 75, as well as processes the broad array of information needed to properly administer 76 the enterprise. Some embodiments will also interact electronically with physicians, employers of exercisers, and in certain cases the insurance carriers 77 of exercisers. In some instances, the enterprise management team is provided both general and medically specific information 74 supporting the continual improvement of the present invention's program and data collection techniques and strategies.

In some embodiments of the present invention, the centralized automated processing of information, privacy control, medical risk management, and solid state equipment 40 design are treated as one integrated administrative system 60,

70. Furthermore, in some embodiments, the exerciser is largely oblivious to the central system that supports the plurality of solid state machines 40 and the fitness trainers that comprise this exercise program. In such embodiments, the exerciser 10 only sees personal exercise results that are displayed on the electronic display located on the equipment 40.

FIGS. 6A-6J illustrate the results for ten different exercisers that have used the systems and methods of the present invention. For each exerciser, the amount of force the exerciser was able to apply in each of four different isometric contraction exercises (bench press, leg press, bent row, and dead lift) during specific exercise sessions is graphically displayed. Furthermore, the recommended amount of recovery time (e.g., less than a week of rest, 1 week of rest, 2 weeks of rest, 3, weeks of rest, 4 weeks of rest) between exercise sessions is given. Further, forward looking advice computed using the algorithms of the present invention are provided. Details of one such algorithm are provided below.

Exemplary algorithm for computing recovery time and forward looking advise. The exemplary algorithm described here is a compendium of discreet elements (feedback options) to aid the exerciser. These feedback options are displayed on the exerciser's printout of exercise results (e.g., FIGS. 6A-6J) and/or on their log in screen. The user's exercise data is analyzed to dictate which feedback option is appropriate. Data considered to select a specific feedback option is (i) the results of last results from the bench press (B), leg press (L), deadlift (D), and bench row (R) isometric contraction exercises and (ii) whether progress was made or not in these specific four exercises in terms of the amount of force exerted. In the tables below, "x" means that progress has been made in a particular isometric contraction exercise during the last exercise session relative to the exercise session just prior to the last exercise session. Further, "o" indicates that no progress has been made in a particular isometric contraction exercise in the last exercise session relative to the exercise session just prior to the last exercise session.

| Feedback option No. 1. | | | |
|---|---|---|---|
| B | L | D | R |
| x | x | x | x |

The message to the exerciser is: "[y]ou are making great progress in all exercises, this indicates that the time between repeating the same exercise and the time for your entire system to recover and finish tissue fortification is at the proper level. Please note that progress like this may continue for weeks, or possibly progress will slow down. Assuming that there is a slow down in your near future, it only means that you are building muscle and the larger muscles need a longer period of time to recover."

The suggestion to the exerciser is to stay on the current recovery schedule.

| Feedback option No. 2. | | | |
|---|---|---|---|
| B | L | D | R |
| o | x | x | x |

The message to the exerciser is: "[y]ou are making progress in all exercises with the exception of the Bench Press. This could simply mean for one reason or another you had less than perfect form in the exercise, possibly you did some exhausting activity with the Bench Press target muscle groups which would pre-exhaust you, or even that your mind may have not been as focused on the task at hand as in previous exercise sessions. No matter the reason for this lack of progress, as it is only one out of the four, and it is likely an anomaly which doesn't necessarily indicate overtraining."

The suggestion to the exerciser is to stay on current recovery schedule.

| Feedback option No. 3. | | | |
|---|---|---|---|
| B | L | D | R |
| x | o | x | x |

The message to the exerciser is: "[y]ou are making progress in all exercises with the exception of the Leg Press. This could simply mean for one reason or another you had less than perfect form in the exercise, possibly you did some exhausting activity with the Leg Press target muscle groups which would pre-exhaust you, or even that your mind may have not been as focused on the task at hand as in previous exercise sessions. No matter the reason for this lack of progress, as it is only one out of the four exercises, and is likely an anomaly, which doesn't necessarily indicate overtraining."

The suggestion to the exerciser is to stay on current recovery schedule.

| Feedback option No. 4. | | | |
|---|---|---|---|
| B | L | D | R |
| x | x | o | x |

The message to the exerciser is: "[y]ou are making progress in all exercises with the exception of the Deadlift. This could simply mean for one reason or another you had less than perfect form in the exercise, possibly you did some exhausting activity with the Deadlift target muscle groups which would pre-exhaust you, or even that your mind may have not been as focused on the task at hand as in previous exercise sessions. No matter the reason for this lack of progress, as it is only one out of the four exercises, and is likely an anomaly, which doesn't necessarily indicate overtraining."

The suggestion to the exerciser is to stay on current recovery schedule.

| Feedback option No. 5. | | | |
|---|---|---|---|
| B | L | D | R |
| x | x | x | o |

The message to the exerciser is: "[y]ou are making progress in all exercises with the exception of the Bent Row. This could simply mean for one reason or another you had less than perfect form in the exercise, possibly you did some exhausting activity with the Bent Row target muscle groups which would pre-exhaust you, or even that your mind may have not been as focused on the task at hand as in previous exercise sessions. No matter the reason for this lack of progress, as it is only one out of the four exercises, and is likely an anomaly, which doesn't necessarily indicate overtraining."

The suggestion to the exerciser is to stay on current recovery schedule.

| Feedback option No. 6. | | | |
|---|---|---|---|
| B | L | D | R |
| o | o | x | x |

The message to the exerciser is: "[y]ou are making progress in all of your pulling exercises, however your Pushing exercises are lagging. This could mean a few things, but the highest probability is that you were just having an off day. It is unlikely that this would indicate overtraining as the pulling exercises are progressing, and more importantly the muscle groups used in the leg press are the largest ones in the body they are usually the last ones to show resource overtraining."

The suggestion to the exerciser is to stay on current recovery schedule.

| Feedback option No. 7. | | | |
|---|---|---|---|
| B | L | D | R |
| o | x | o | x |

The message to the exerciser is: "[y]ou are making progress in the Leg Press and in the Row, however no progress in the Bench Press and the Deadlift. The most likely explanation for this is either multiple location specific issues, as in a sore shoulder and a pain in the lower back. This pattern is both unlikely and not indicative of overtraining Your advisor should take note of this lack or progress and take special care to observe your exercise form."

The suggestion to the exerciser is to stay on current recovery schedule.

| Feedback option No. 8. | | | |
|---|---|---|---|
| B | L | D | R |
| o | x | x | o |

The message to the exerciser is: "[y]ou are making progress in the Leg Press and in the Deadlift, however no progress in the Bench Press and the Row. This could be an indication of localized overtraining Both the Bench Press and the Row use much smaller muscle groups than the Deadlift and Leg Press do. Therefore you may be doing something in everyday life that is exhausting your upper-body and thereby halting potential development. Unless you feel that this is an anomaly caused by poor form or a lack of focus it is advisable that you take more time to recover between exercise sessions."

The suggestion to the exerciser is to add extra recovery time into the exercise schedule.

| Feedback option No. 9. | | | |
|---|---|---|---|
| B | L | D | R |
| x | o | o | x |

The message to the exerciser is: "[y]ou are making progress in the Bench Press and in the Row, however no progress in the Leg Press and the Deadlift. This isn't necessarily a common situation due to the Leg Press and Deadlift utilizing larger muscle groups, they are usually the last groups to indicate overtraining This situation doesn't indicate overtraining and could possibly indicate a back soreness or injury. If this trend continues it would be advisable to look at some of the activities that you partake in during an average week that could be exhausting your lower body."

The suggestion to the exerciser is to stay on current recovery schedule.

| Feedback option No. 10. | | | |
|---|---|---|---|
| B | L | D | R |
| x | o | x | o |

The message to the exerciser is: "[y]ou are making progress in the Bench Press and in the Deadlift, however no progress in the Leg Press and the Row. This isn't necessarily a common situation and it is not possible that these two things are connected. It is possible that your general energy level is down and you are not in the best frame of mind when exercising. This situation doesn't look to be overtraining and you should maintain your present schedule of exercise."

The suggestion to the exerciser is to stay on current recovery schedule.

| Feedback option No. 11. | | | |
|---|---|---|---|
| B | L | D | R |
| x | x | o | o |

The message to the exerciser is: "[y]ou are making progress in all of your Push exercises, however your Pull exercises are lagging. This could mean a few things, but the highest probability is that you were just having an off day. It is unlikely that this would indicate overtraining as the pulling exercises are progressing, and more importantly the muscle groups used in the leg press are the largest ones in the body they are usually the last ones to show resource overtraining."

The suggestion to the exerciser is to stay on current recovery schedule.

| Feedback option No. 12. | | | |
|---|---|---|---|
| B | L | D | R |
| x | o | o | o |

The message to the exerciser is: "[y]ou are only making progress in the Bench Press. This could indicate getting over an illness or possibly a general lack of energy for one reason or another, however this most likely means that you are overtraining It would be advisable that you add more time between your exercise sessions. This will give you more time to recover, and enable you to make progress once both initial recovery and tissue fortification have taken place."

The suggestion to the exerciser is to add extra recovery time into the exercise schedule.

| Feedback option No. 13. | | | |
|---|---|---|---|
| B | L | D | R |
| o | x | o | o |

The message to the exerciser is: "[y]ou are only making progress in the Leg Press. This could indicate getting over an illness or possibly a general lack of energy for one reason or another, however this most likely means that you are overtraining It would be advisable that you add more time between your exercise sessions. This will give you more time to recover, and enable you to make progress once both initial recovery and tissue fortification have taken place."

The suggestion to the exerciser is to add extra recovery time into the exercise schedule.

| Feedback option No. 14. | | | |
|---|---|---|---|
| B | L | D | R |
| o | o | x | o |

The message to the exerciser is: "[y]ou are only making progress in the Deadlift. This could indicate getting over an illness or possibly a general lack of energy for one reason or another, however this most likely means that you are overtraining It would be advisable that you add more time between your exercise sessions. This will give you more time to recover, and enable you to make progress once both initial recovery and tissue fortification have taken place."

The suggestion to the exerciser is to add extra recovery time into the exercise schedule.

| Feedback option No. 15. | | | |
|---|---|---|---|
| B | L | D | R |
| o | o | o | x |

The message to the exerciser is: "[y]ou are only making progress in the Row. This could indicate getting over an illness or possibly a general lack of energy for one reason or another, however this most likely means that you are overtraining It would be advisable that you add more time between your exercise sessions. This will give you more time to recover, and enable you to make progress once both initial recovery and tissue fortification have taken place."

The suggestion to the exerciser is to add extra recovery time into the exercise schedule.

| Feedback option No. 16. | | | |
|---|---|---|---|
| B | L | D | R |
| o | o | o | o |

The message to the exerciser is: "[y]ou are not making progress in any of the exercises. This is usually simply an indication of overtraining, all that is necessary is to allow for both the entire body system and the specific muscles longer to go through the initial recovers, then through the tissue fortification phase."

The suggestion to the exerciser is to add extra recovery time into the exercise schedule.

When an exerciser takes a week off that isn't necessarily scheduled, or adds a week of rest time in between workouts, the analysis of the first time exercising after the break must only look at the current session in comparison to what was done in the session before where the same exercises were performed. For example, if an exerciser is on the split program where the exerciser does the Push exercises one week, then the Pull the following week, and then takes a vacation and skips a week, analysis of exercises that took place before the vacation would ignore the excess recovery variable, and hence should not be considered.

| After extra recovery time, option No. 1. | | | |
|---|---|---|---|
| B | L | D | R |
| — | — | x | x |

The message to the exerciser is: "[y]ou are making progress in both the Deadlift and in the Row. As the recovery variables have changed since your last Push session there is no need to analyze those results."

The suggestion to the exerciser is to stay on current recovery schedule.

| After extra recovery time, option No. 2. | | | |
|---|---|---|---|
| B | L | D | R |
| — | — | o | x |

The message to the exerciser is: "[y]ou are making progress in the Row, however not in the Deadlift. This most likely means you have some injury that possibly you aren't completely aware of This would indicate that you are compensating while you are doing the Deadlift and that is keeping you from taking the exercise to failure. The Deadlift must be paid close attention to the next time you do it to take special note of your exercise form. As the recovery variables have changed since your last Push session there is no need to analyze those results."

The suggestion to the exerciser is to stay on current recovery schedule.

| After extra recovery time, option No. 3. | | | |
|---|---|---|---|
| B | L | D | R |
| — | — | o | o |

The message to the exerciser is: "[y]ou did not make progress in your Pull exercises. As you have just had extra recovery time overtraining is not likely, however IS a possibility. It is recommended that you continue on your prescribed schedule unless this lack of progress continues to your next session. In that case a clear indication of overtraining will be made and you must add more time between exercise sessions. As the recovery variables have changed since your last Push session there is no need to analyze those results."

The suggestion to the exerciser is to stay on current recovery schedule.

| After extra recovery time, option No. 4. | | | |
|---|---|---|---|
| B | L | D | R |
| x | x | — | — |

The message to the exerciser is: "[y]ou are making progress in both the Bench Press and in the Leg Press. As the recovery variables have changed since your last Pull session there is no need to analyze those results.

The suggestion to the exerciser is to stay on current recovery schedule.

| After extra recovery time, option No. 5. | | | |
|---|---|---|---|
| B | L | D | R |
| o | x | — | — |

The message to the exerciser is: "[y]ou are making progress in the Bench Press, however not in the Leg Press. This most likely means you have some injury, that you possibly you aren't completely aware of. This would indicate that you are compensating for while you are doing the Bench Press that is keeping you from taking the exercise to failure. The Bench Press must be paid close attention to the next time you do it to take special note of your exercise form. As the recovery variables have changed since your last Pull session there is no need to analyze those results."

The suggestion to the exerciser is to stay on current recovery schedule.

| After extra recovery time, option No. 6. | | | |
|---|---|---|---|
| B | L | D | R |
| o | o | — | — |

The message to the exerciser is: "[y]ou did not make progress in your Push exercises. As you have just had extra recovery time overtraining is not likely, however IS a possibility. It is recommended that you continue on your prescribed schedule unless this lack of progress continues to your next session. In that case a clear indication of overtraining will be made and you must add more time between exercise sessions. As the recovery variables have changed since your last Pull session there is no need to analyze those results."

The suggestion to the exerciser is to stay on current recovery schedule.

Additional Exemplary embodiments. Embodiments of the present invention involving an automated health risk managed system for physical development, also referred to as an "exercise program and administrative system," have been described above. What follows is more description of such systems and methods as well as optional embodiments encompassing the same.

In general, the systems and methods of the present invention employ a science based, solid state, data driven physical development technology program that provides interested parties, referred by physicians, and others, in selected locations, a novel and inherently safer method of fitness and strength training/testing. Primary health risk factors are used to screen for unacceptable injury risk, both initially and on an ongoing basis. For those exercisers that satisfy these pre-screen tests, highly accurate and repeatable strength test results are derived in a private setting with a personal trainer. Such results are transmitted, preferably in an encrypted manner, and analyzed by a central processor. Such analysis allows for a scientifically based incremental development program maximizing the balance between sufficient muscle stress for stimulating muscle development/strength and the optimal muscle tissue recovery time period needed between ongoing isometric training sessions.

The present invention provides an exceedingly safe, life long, health fitness and strength building exercise system. In some embodiments of the invention, there is an enterprise wide system of custom designed fitness equipment and custom designed software. The equipment is of a solid state design, with no moving parts, virtually eliminating traditional fitness equipment related exerciser injuries. The centralized software utilizes highly accurate medical information and highly accurate fitness equipment data collected from each exerciser, to analyze, plan, manage, and report to each exerciser their progress against pre-stated goals, thereby maintaining their interest and life long commitment to better health through improved strength and fitness.

In some embodiments, the present invention provides a closed loop, fully integrated, and complete health and fitness solution including an exercise program and administrative system to support a medical science based injury avoidance and long term strength building enterprise. In some instances, this embodiment provides a model by which high levels of equipment utilization, limited floor space, and a highly distributed system effectively reach larger populations of maturing adults. It also may have a highly structured data collection and processing capability, allowing more and more science based analysis of trends among larger and larger populations of exercisers, consistently resulting in improved analysis at the individual exerciser level.

Some embodiments of the present invention provide servers that mirror other servers, thereby protecting all enterprise data in a manner that could not be achieved economically without the plurality of sites connecting via a network to a central data center. Some embodiments of the present invention also provide a health science based service that can be supported by employers and insurance carriers as part of their commitment to improved preventative medical care for a maturing population.

Another aspect of the present invention is its family of solid state fitness machines that constitute a training/testing subsystem, utilizing non injury designs, and strain gauges for force measuring and data collection, combined with a personal trainer in a private setting, providing the proper medical focus on all aspects of the present invention. In some instances, the data collection is highly accurate and highly reproducible, allowing precise analysis and reporting of incremental progress, providing long term progress reporting against specifically stated goals, and permitting modulation of each exercisers recovery process.

In addition, some embodiments of the present invention include custom built exercise machines, employing no moving components, thereby eliminating equipment failures that often result when traditional fitness equipment is utilized in typical fitness centers. In some cases, the present invention may also have enclosed adjusting mechanisms to accommodate differing anatomical characteristics of exercisers without allowing exercisers any access to adjusting mechanisms and thereby avoiding injury. In some instances, the adjusting mechanisms may have been load tested and calibrated to automatically compensate for every exerciser's anatomical differences, such that the performance parameters measured remain accurate, allowing scientifically accepted practices to be employed in the analyses performed for each exerciser, and the utilization of all data from the plurality of exercisers to be used in broad based group/type analysis. The present invention may also have a simple equipment design that precludes an exerciser from making an error resulting in injury. The invention may also only have concentric isometric loading that thereby eliminates eccentric contraction and associated injuries.

In some cases, the present invention's solid state design eliminates the potential for stored energy so that the exerciser can only experience loads or forces that they alone apply with that energy immediately and completely dissipating once the voluntary contraction ceases. In other instances, the solid state design does not permit any load to be applied to an exerciser that the exerciser cannot handle, because the load/force applied is applied by the exerciser.

Some embodiments of the present invention provide a plurality of solid state machines, all of which are new in design concept, and utilize highly accurate training/testing measuring technology, not associated with traditional workout equipment. It may also include highly accurate load cells to measure exerciser applied forces, times, and cycles, resulting in accurate data from a plurality of exercisers to be processed for further use in adjusting an exercisers fitness program and prescribed recovery schedule.

Some embodiments of the present invention provide customized exerciser programs to meet physician objectives, as well as exerciser goals. In some instances, the invention also has the ability to eliminate a full range of motion and the injuries that typically result from traditional full range of motion fitness equipment. The equipment may also have the capacity to work all major muscle groups and thereby accomplish a full body workout bring the major muscle groups to failure.

In some embodiments of the present invention, encrypted medical data, exercise data, and administrative information necessary to support the exercise program is communicated via a network. Some embodiments of the present invention also include the consistent application of equipment and technology among a plurality of sites thereby allowing any individual exerciser to utilize any machine at any location and generate training/testing results that are equipment and site independent, thus permitting individuals to engage in the program of the present invention irrespective of where they may be located at any particular time.

Another aspect of the present invention is the automated and centralized enterprise wide processing center system, also referred to herein as the "central system", that provides privacy for exerciser medical information, disciplined analysis of exercise data, and accurate reporting to each exerciser of progress in the program, while at the same time allowing for an information management system providing all information and data services required for the efficient and successful operation of the enterprise.

In some instances, the central system has the feature of receiving via a network all of the encrypted medical data, exercise data, and administrative information necessary to support the methods of the present invention. It may also have the capacity to store encrypted medical files as well as extracted files and to interface with the operating system data management to support processing and reporting. The central system may also include an electronic prescreening feature as one element of the user interface for every exerciser appointment, further assuring that an exerciser cannot proceed without meeting certain designated health preconditions. Furthermore, the central system may also have the capacity to process exerciser health information, and training/testing data creating an exerciser specific fitness program, providing exerciser reports used to define safety constraints and goals for future exercise and recovery.

In addition, in some embodiments, the central system has the critical capability of calculating the prescribed recovery period for each separate exerciser, based on personalized data balanced against experience trends measured among other exercisers with various similar characteristics, such as health conditions, age, and gender among many characteristics. Moreover, the central system may also have the capacity, based on data base information, displayed on a user interface, to provide each exerciser with comments, on incremental fitness progress, as well as against long term goals. In some cases, the central server can also generate graphical displays showing incremental, and long term progress in terms that are understandable and comparable over years of strength building and strength maintenance.

Another feature of the central system is the capacity of providing to a plurality of sites, and designated centralized locations, the enterprise wide management information required for efficient operation, and compliance with standard medical practices, and laws affecting the business operations. In some cases, the present invention also includes interactive electronic information tools available at a plurality of sites as well as designated centralized business functions, the administrative information essential to operating an enterprise with centralized processing and distributed operations.

Yet another feature of the central system is the presence of a network of sites connected to a server based family of computer programs that avoid the unreasonable maintenance burden that would exist if a plurality of sites were required to install and maintain operational programs locally. In some cases the plurality of sites may be able to access the centralized support services for updates, and operations changes via a browser.

Another aspect of the central server is its ability to utilize the highly accurate strain gauge measurement data to calculate accurate results with precision. In addition, the central server may also be able to monitor participation in and compliance with a prescribed (by a physician) and/or paid for program of exercise (by an employer or other interested party) thereby providing accurate and ongoing feedback to those interested parties responsible for the physical and/or financial support of the exerciser.

In some embodiments, the central server may also include the necessary accounting and billing functions required for billing employers, insurance carriers, individual exercisers, and other parties. In some instances, the central server will also have the necessary functional interfaces to support automatic credit card debiting and Automated Clearing House (ACH) electronic funds transfers to facilitate all billing of exercisers for services and goods, eliminating the need for any personal trainer and his/her exerciser to become involved personally in any financial transactions at a plurality of sites. The central server may also include additional financial functions necessary for full support of accounting, enterprise finance, regulatory compliance and general enterprise administration.

In some embodiments, the central server health information collection sub-system that prescreens each exerciser before any exercises are performed, to determine the exerciser's suitability for the program and to provide specific constraints that any particular exerciser may require to maintain safety. In some instances, the automated central system provides privacy for medical data, and access for incremental exerciser data, to support the processing and reporting of progress against goals, and prescribed recovery.

In some instances, medical criteria also determine, define, and/or constrain the appointment by appointment exercise regimens in the present invention and prescribe the appropriate recovery period for each individual exerciser. In some examples, the exercise regimen is unique to the exerciser and not selected from a family of standard programs. The present invention may also have an online video support feature in the form of help, and training/testing results, for both the exerciser and the personal trainer assisting the exerciser.

The present invention also includes services offered to physicians and their patients, to specifically define pre-operative strength building programs as an aid to facilitating post operative recovery. In other embodiments, the present invention includes services that set long-term exerciser goals that can be met over a period of years, thereby avoiding the exceedingly short-term commitments exercisers have demonstrated when using traditional fitness industry equipment, facilities, and programs.

CONCLUSION

Although the detailed description contains many specifics, these should not be construed as limiting the scope of the present invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents.

The present invention can be implemented as a computer program product that comprises a computer program mechanism embedded in a computer readable storage medium. For instance, the computer program product could contain the program modules of FIG. 5. These program modules can be stored in a CD-ROM, DVD, magnetic disk storage product, or any other computer readable data or program storage product. The software modules in the computer program product may also be distributed electronically, via the Internet or otherwise, by transmission of a computer data signal (in which the software modules are embedded) on a carrier wave.

No element, component or method step is intended to be dedicated to the public regardless of whether the element, component or method step is explicitly recited in the claims.

What is claimed is:

1. A computer system for facilitating a fully contracted exercise regimen for a subject, the computer system comprising:
   a central processing unit;
   a memory, coupled to the central processing unit, the memory storing a computer program mechanism, the computer program mechanism comprising:
   (A) instructions for receiving medical health information of a subject enrolled in the fully contracted exercise regimen comprising a plurality of fully contracted exercises, wherein each fully contracted exercise in the plurality of fully contracted exercises places stress on a fully contracted muscle group of the subject;
   (B) instructions for developing one or more exercise constraints as a function of the medical health information of said subject;
   (C) instructions for receiving an exercise result from the plurality of fully contracted exercises that were performed by said subject using solid-state exercise equipment in the presence of a fitness trainer, wherein said solid state exercise equipment has a strain gauge in order to impose or monitor exercise constraints in said one or more exercise constraints and wherein data from the strain gauge is found in said exercise result;
   (D) instructions for creating a mandatory recovery period for said subject during which time said subject does not perform said plurality of fully contracted exercises, wherein said mandatory recovery period is a function of the exercise result received in (C);
   (E) instructions for developing a new set of one or more exercise constraints that are refined based upon the exercise result received in (C); and
   (F) instructions for repeating said instructions for receiving (C) and said instructions for creating (D) using a the new set of one or more exercise constraints.

2. The computer system of claim 1, wherein an exercise constraint in said one or more exercise constraints is an amount of force that can be used in a fully contracted exercise in said plurality of fully contracted exercises.

3. The computer program product of claim 1, wherein an exercise constraint in said one or more exercise constraints is a maximum number of repetitions of a fully contracted exercise in said plurality of fully contracted exercises.

4. The computer system of claim 1, wherein said mandatory recovery time is a function of the exercise result.

5. The computer system of claim 4, wherein said exercise result is a length of time that said subject was able to exert a force during a fully contracted exercise in the plurality of fully contracted exercises.

6. The computer system of claim 4, wherein said exercise result is an amount of force that said subject was able to exert during a fully contracted exercise in said plurality of fully contracted exercises.

7. The computer system of claim 1, wherein the plurality of fully contracted exercises that were performed by said subject were accomplished in five minutes or less.

8. The computer system of claim 1, wherein said fully contracted exercise regimen works a plurality of muscle groups thereby accomplishing a full body workout.

9. The computer system of claim 1, wherein a fully contracted exercise in said plurality of fully contracted exercises stresses a muscle group to a point of failure.

10. The computer system of claim 1, the computer program mechanism further comprising instructions for receiving all or a portion of the exercise constraints and exercise results in an encrypted manner.

11. The computer system of claim 1, wherein a length of time of the mandatory recovery period is a function of said exercise result and an experience trend measured among other subjects that use said fully exercise regimen, wherein said other subjects have one or more characteristics in common with said subject.

12. The computer system of claim 10, wherein a characteristic in said one or more characteristics is a health condition, an age, or a gender.

13. The computer system of claim 1, the computer program mechanism further comprising:
    instructions for receiving accounting and billing information relating to said fully contracted exercise regimen for said subject.

14. The computer system of claim 1, the computer program mechanism further comprising:
    instructions for receiving, over a network, all encrypted medical data, exercise data, and administrative information relating to said subject.

15. The computer system of claim 1, the computer program mechanism further comprising:
    one or more encrypted medical files associated with said subject.

16. The computer system of claim 1, the computer program mechanism further comprising:
    instructions for receiving said medical health information, said exercise result from any one or more of a plurality of remote sites.

17. The computer program product of claim 1, wherein an exercise constraint in said one or more exercise constraints is a maximum force of a fully contracted exercise in said plurality of fully contracted exercises.

18. The computer program product of claim 3, wherein the number of repetitions is one and a maximum amount of force is applied a single time during the fully contracted exercise in the plurality of fully contracted exercises.

* * * * *

UNITED STATES PATENT AND TRADEMARK OFFICE
CERTIFICATE OF CORRECTION

Page 1 of 1

PATENT NO. : 7,775,937 B2
APPLICATION NO. : 12/533607
DATED : August 17, 2010
INVENTOR(S) : Jaquish et al.

It is certified that error appears in the above-identified patent and that said Letters Patent is hereby corrected as shown below:

On title page please add Item (62):

Patent 7,775,937 is a divisional Application of Patent 7,753,825 (U.S. Application 11/254,289) issued on July 13, 2010.

Signed and Sealed this
Twenty-first Day of February, 2012

David J. Kappos
*Director of the United States Patent and Trademark Office*